US009341563B2

(12) United States Patent  
Amari

(10) Patent No.: US 9,341,563 B2  
(45) Date of Patent: May 17, 2016

(54) AGGREGATE BOARD, LIGHT EMITTING DEVICE, AND METHOD FOR TESTING LIGHT EMITTING ELEMENT

(71) Applicant: NICHIA CORPORATION, Anan-shi, Tokushima (JP)

(72) Inventor: Koichi Amari, Anan (JP)

(73) Assignee: NICHIA CORPORATION, Anan-shi (JP)

( * ) Notice: Subject to any disclaimer, the term of this patent is extended or adjusted under 35 U.S.C. 154(b) by 0 days.

(21) Appl. No.: 14/579,085

(22) Filed: Dec. 22, 2014

(65) Prior Publication Data

US 2015/0185137 A1 Jul. 2, 2015

(30) Foreign Application Priority Data

Dec. 27, 2013 (JP) .................................. 2013-273533  
Aug. 20, 2014 (JP) .................................. 2014-167471

(51) Int. Cl.
*H01L 33/50* (2010.01)  
*H01L 33/62* (2010.01)  
(Continued)

(52) U.S. Cl.
CPC ............ *G01N 21/25* (2013.01); *G01N 21/8806* (2013.01); *H01L 33/62* (2013.01);  
(Continued)

(58) Field of Classification Search
CPC ....... H01L 33/54; H01L 33/62; H01L 33/486; H01L 33/505; H01L 33/507; H01L 33/508; H05K 1/0298; H05K 1/0306; G01N 21/25; G01N 21/8806  
USPC ............... 257/3.88, 89, 98, 369, 759, E33.06, 257/E33.056, E33.059, E27.07, E27.105, 257/E21.003, E21.244; 438/26, 29, 381, 438/382; 356/237.1; 174/251  
See application file for complete search history.

(56) References Cited

U.S. PATENT DOCUMENTS

2004/0084777 A1* 5/2004 Yamanoue .......... H01L 23/5227  
257/758  
2006/0113540 A1* 6/2006 Furuya .............. G02F 1/133553  
257/59

(Continued)

FOREIGN PATENT DOCUMENTS

DE 102011056708 A1 6/2013  
EP 2398072 A1 12/2011

(Continued)

OTHER PUBLICATIONS

Extended European Search Report of the corresponding European Patent Application No. 14200076.9, dated May 28, 2015.

*Primary Examiner* — Dao H Nguyen  
(74) *Attorney, Agent, or Firm* — Global IP Counselors, LLP

(57) ABSTRACT

An aggregate board, comprising: an insulator having a front face and a rear face; a pair of a first front face wiring pattern and a second front face wiring pattern, a plurality of which are arranged on the front face of the insulator; a pair of a first rear face wiring pattern and a second rear face wiring pattern, a plurality of which are arranged on the rear face of the insulator; at least one first inner layer wiring pattern that is separated from the second front face wiring pattern and the second rear face wiring pattern, that is connected to the first front face wiring pattern and the first rear face wiring pattern, and that extends in a first direction in an interior of the insulator; at least one second inner layer wiring pattern that is separated from the first front face wiring pattern and the first rear face wiring pattern, that is connected to the second front face wiring pattern and the second rear face wiring pattern, and that has a part that extends in a second direction which is different from the first direction, in the interior of the insulator; and the first inner layer wiring pattern and the second inner layer wiring pattern being positioned in the same layer.

20 Claims, 11 Drawing Sheets

(51) Int. Cl.
  *H01L 33/58* (2010.01)
  *G01N 21/25* (2006.01)
  *G01N 21/88* (2006.01)
  *H01L 33/48* (2010.01)
  *H01L 33/54* (2010.01)
  *H01L 25/075* (2006.01)

(52) U.S. Cl.
  CPC ...... *G01N2201/02* (2013.01); *G01N 2201/062* (2013.01); *H01L 25/0753* (2013.01); *H01L 33/486* (2013.01); *H01L 33/50* (2013.01); *H01L 33/54* (2013.01); *H01L 2224/16225* (2013.01); *H01L 2924/0002* (2013.01); *H01L 2933/0041* (2013.01); *H01L 2933/0066* (2013.01)

(56) References Cited

U.S. PATENT DOCUMENTS

| | | |
|---|---|---|
| 2011/0018026 A1 | 1/2011 | Konno et al. |
| 2011/0233505 A1* | 9/2011 | Nitta ............... H01L 27/24 257/3 |
| 2011/0291154 A1 | 12/2011 | Noichi et al. |
| 2012/0056217 A1* | 3/2012 | Jung ............... H01L 25/0753 257/89 |
| 2012/0248483 A1 | 10/2012 | Beppu et al. |
| 2014/0299911 A1 | 10/2014 | Zitzlsperger |
| 2014/0346548 A1 | 11/2014 | Beppu et al. |

FOREIGN PATENT DOCUMENTS

| | | |
|---|---|---|
| JP | 09-275274 A | 10/1997 |
| JP | 2003-078170 A | 3/2003 |
| JP | 2006-216764 A | 8/2006 |
| JP | 2009-164311 A | 7/2009 |
| JP | 2009-260244 A | 11/2009 |
| JP | 2010-182981 A | 8/2010 |
| JP | 2012-256848 A | 12/2012 |

* cited by examiner

AGGREGATE BOARD, LIGHT EMITTING DEVICE, AND METHOD FOR TESTING LIGHT EMITTING ELEMENT

CROSS-REFERENCE TO RELATED APPLICATIONS

This application claims priority to Japanese Patent Applications No. 2013-273533 filed on 27 Dec. 2013 and No. 2014-167471 filed on 20 Aug. 2014. The entire disclosure of Japanese Patent Applications No. 2013-273533 and No. 2014-167471 is hereby incorporated herein by reference.

BACKGROUND

1. Technical Field

The present disclosure relates to an aggregate board, a light emitting device, and a method for testing a light emitting element.

2. Description of the Related Art

In general, a light emitting device featuring a light emitting element such as a light emitting diode (LED) is made up of light emitting elements, protective elements, and other such electronic parts, and a board on which these are disposed. The light emitting elements may also be covered with a translucent resin containing a fluorescent material in order to protect the light emitting elements, protective elements, and so forth, and to make the light emitting elements emit light of a specific color.

To this end, after a light emitting element is made into a chip, the light emitting elements are mounted on a board equipped with wiring patterns, terminals, etc. The board used here is such that the front face, the interior, and/or the rear face is provided with a conductor material that will serve as a pair of wiring patterns or terminals, as a continuous pattern corresponding to a plurality of light emitting devices. The board on which the light emitting elements have been mounted is finally split up into individual light emitting elements, or into groups of a particular number of light emitting elements, to complete a light emitting device.

The light emitting devices thus obtained are individually checked for illuminating and adjusted for color.

Meanwhile, JP2003-78170A proposes a testing method and a testing structure for a light emitting device which either does not light or has uneven brightness prior to the light emitting device being made into a finished product.

With this proposed testing structure, and a board equipped with this testing structure, a separate structure is provided for the purpose of testing, and when light emitting diodes are made into a chip, testing cannot be carried out unless the light emitting elements are mounted on a board along with a testing structure through an extremely complicated process, such as one in which the light emitting elements are transferred from a board used for primary storage, a via hole is formed in this board, and extension wiring pattern is formed on the light emitting element electrodes.

SUMMARY

In light of this situation, there has been a need for a method with which light emitting elements can be individually lighted, and the color of the light emitting elements can be individually measured, before the board is split up into individual light emitting devices, in a state in which a plurality of light emitting elements have been mounted on an aggregate board used for forming light emitting devices, and with which this can be accomplished easily, without entailing any special steps.

The present disclosure was conceived in light of the above problem, and it is an object thereof to provide an aggregate board with which light emitting elements can be individually lighted, and the color of the light emitting elements can be individually measured, before the board is split up into individual light emitting devices, in a state in which a plurality of light emitting elements have been mounted, as well as a light emitting device and a testing method in which this aggregate board is used.

The present disclosure relates to aggregate boards, a light emitting device and a method for testing a light emitting element.

One embodiment of the aggregate board includes:

an insulator having a front face and a rear face;

a pair of a first front face wiring pattern and a second front face wiring pattern, a plurality of which are arranged on the front face of the insulator;

a pair of a first rear face wiring pattern and a second rear face wiring pattern, a plurality of which are arranged on the rear face of the insulator;

at least one first inner layer wiring pattern that is separated from the second front face wiring pattern and the second rear face wiring pattern, that is connected to the first front face wiring pattern and the first rear face wiring pattern, and that extends in a first direction in an interior of the insulator;

at least one second inner layer wiring pattern that is separated from the first front face wiring pattern and the first rear face wiring pattern, that is connected to the second front face wiring pattern and the second rear face wiring pattern, and that has a part that extends in a second direction which is different from the first direction, in the interior of the insulator; and the first inner layer wiring pattern and the second inner layer wiring pattern being positioned in the same layer.

Another embodiments of the aggregate board, includes:

an insulator having a front face and a rear face;

a pair of a first front face wiring pattern and a second front face wiring pattern, a plurality of which are arranged on the front face of the insulator;

a pair of a first rear face wiring pattern and a second rear face wiring pattern, a plurality of which are arranged on the rear face of the insulator;

at least one first inner layer wiring pattern that is separated from the second front face wiring pattern and the second rear face wiring pattern, that is connected to the first front face wiring pattern and the first rear face wiring pattern, and that extends in a first direction in an interior of the insulator;

at least one second inner layer wiring pattern that is separated from the first front face wiring pattern and the first rear face wiring pattern, that is connected to the second front face wiring pattern and the second rear face wiring pattern, and that has a part that extends in a second direction, which is different from the first direction, in the interior of the insulator; and the first rear wiring pattern and the second rear wiring pattern each having wide regions at both ends.

One embodiment of the light emitting device, includes:

a board having a plurality of wiring patterns and an insulator having a front face and a rear face;

a light emitting element that is mounted on the board; and a fluorescent material layer that covers the light emitting element, the wiring patterns including;

a pair of a first front face wiring pattern and a second front face wiring pattern disposed on the front face of the insulator;

a pair of a first rear face wiring pattern and a second rear face wiring pattern disposed on the rear face of the insulator;

a first inner layer wiring pattern that is connected to the first front face wiring pattern and the first rear face wiring pattern, and a second inner layer wiring pattern that is connected to the second front face wiring pattern and the second rear face wiring pattern;

the first inner layer wiring pattern and the second inner layer wiring pattern being positioned in the same layer; and the insulator being such that the first inner layer wiring pattern is exposed at a pair of end faces including two opposing edges, and the second inner layer wiring pattern is exposed at a pair of end faces including the other two opposing edges.

One embodiment of the method for testing a light emitting element, includes the steps of:

connecting a plurality of light emitting elements to the pair of first and second front face wirings of the aggregate board according to claim 1; and illuminating at least one light emitting element to test the characteristics of the light emitting element.

DETAILED DESCRIPTION OF THE INVENTION

Figure 1A:
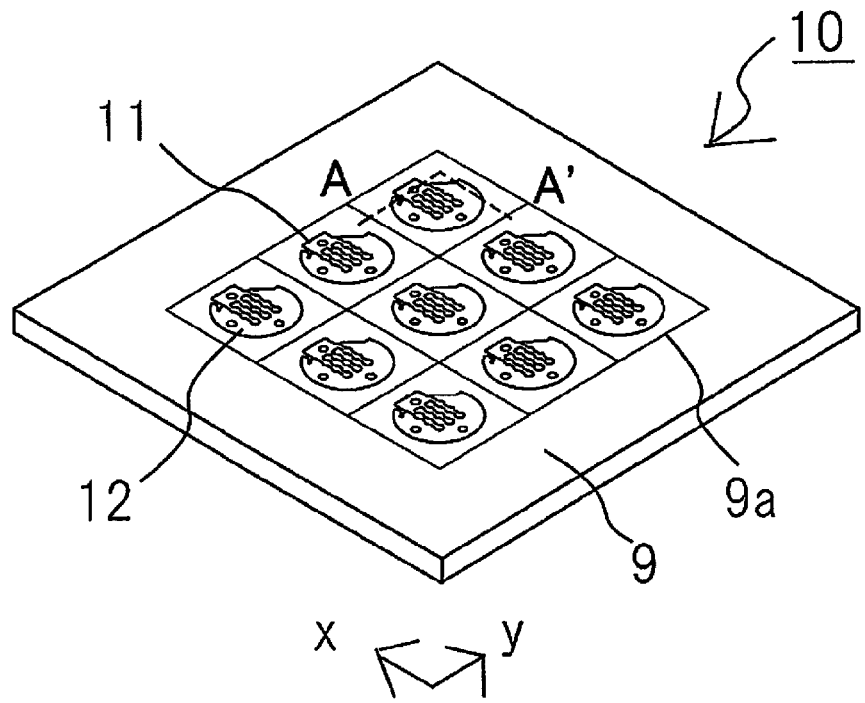
FIG. 1A is a simplified oblique view of an example of the aggregate board of the present disclosure.
Figure 1B:
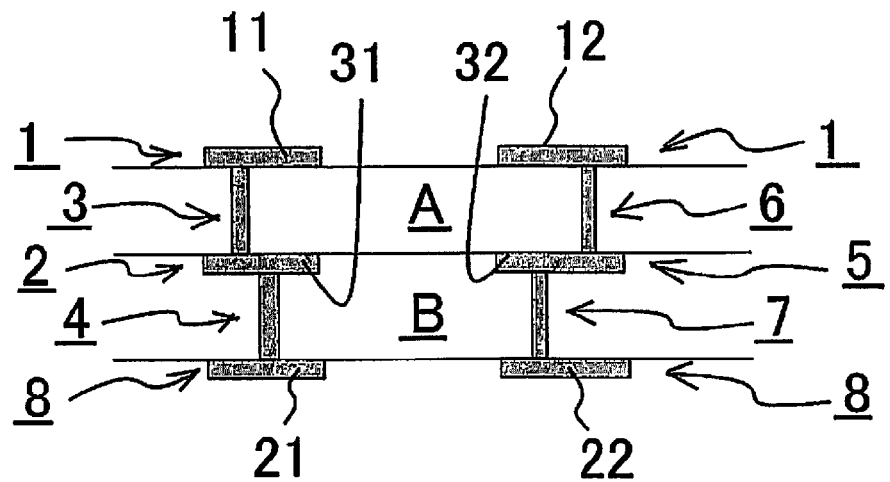
FIG. 1B is a partial cross section along the A-A' line in FIG. 1A.

Embodiments for implementing the light emitting element of the present disclosure will be described below with reference to the accompanying drawings. The sizes and the arrangement relationships of the members in each of drawings are occasionally shown exaggerated for ease of explanation. Further, in the description below, the same designations or the same reference numerals may, in principle, denote the same or like members and duplicative descriptions will be appropriately omitted. In addition, a plurality of structural elements of the present disclosure may be configured as a single part which serves the purpose of a plurality of elements, on the other hand, a single structural element may be configured as a plurality of parts which serve the purpose of a single element. Further, constitutions described in some of examples and embodiments can be employed in other examples and embodiments.

[Aggregate Board]

The aggregate board of the present disclosure includes an insulator having a front face and a rear face, front face wiring patterns, rear face wiring patterns, and inner layer wiring patterns. In this application, these wiring patterns will sometimes be collectively referred to as conductive members. This aggregate board can be used to mount a plurality of semiconductor elements or other such electronic elements, and is particularly advantageous when used to mount light emitting elements. Therefore, to mount the electronic elements more efficiently, the aggregate board preferably has wiring pattern structures that allow for regular wiring pattern to a plurality of electronic elements, such as wiring pattern structures that allow for regular wiring pattern in a first direction and a second direction, and even more preferably has wiring pattern structures that allow for regular wiring pattern in rows and columns.

The "first direction" here may be any direction, but is preferably a direction corresponding to the x axis in two dimensions (such as the row direction). The "second direction" may be a different direction from the first direction, and is preferably a direction corresponding to the y axis in two dimensions (such as the column direction).

(Insulator)

There are no particular restrictions on the insulator as long as it is a material having electrical insulating properties, but it can be formed from ceramics such as alumina, aluminum nitride; glass; glass-epoxy, paper-phenol, paper-epoxy, glass composite, LTCC (low temperature co-fired ceramics); thermoplasticity resin; thermosetting resin and the like, or combination thereof, for example.

There are no particular restrictions on the shape of the insulator, but the outer shape includes the above-mentioned front face and rear face, and the front face and/or rear face is preferably flat. A flat plate with rectangular shape is preferable as the basic shape, for example.

There are no particular restrictions on the thickness or size of the insulator, which can be suitably adjusted according to the size, number, and so forth of the electronic elements to be mounted, and these will correspond to the thickness and size of the aggregate board. For instance, the total thickness may be about 0.3 to 1.0 mm, and the size about 50×50 mm to 100×100 mm.

The insulator is formed integrally in the aggregate board, but is formed as a layer in the manufacturing process of this board, with two or more of these layers being laminated and finally integrated to constitute the aggregate board.

When a ceramic board is used as the insulator, the aggregate board can be manufactured by a post firing, a co-firing, both of these, or another such method. Post firing is a method in which a conductive member is formed on a pre-fired ceramic board of large diameter. Co-firing is a method in which the ceramic board and the conductive member are both fired at the same time. In particular, it is preferable to use post firing to obtain an aggregate board with high dimensional accuracy. When a conductive member is formed by post firing, a fine pattern can be formed by sputtering, vacuum vapor deposition, or another such method involving lift-off featuring photolithography.

An advantage to co-firing is that adhesion is improved between the ceramic board and the conductive member, and the manufacturing cost entailed by firing can be kept lower.

The portion of the conductor that is embedded in the insulator may be formed by co-firing, and then the portions exposed on the front face and rear face of the insulator may be formed by post firing. This ensures good dimensional accuracy and keeps the manufacturing cost down even when the conductive member is embedded in the insulator.

(Conductive Member)

The conductive members are used to electrically connect the light emitting elements to an external power supply, and to apply voltage from the external power supply to the light emitting elements. The conductive members can be formed from any material that is electroconductive, such as a single-layer film or a laminate film of Au (gold), Ag (silver), Cu (copper), W (tungsten), or another such metal or alloy. Part of the conductive member exposed on one side of the insulator can be utilized to dissipate heat from the electronic elements. There are no particular restrictions on the thickness of the conductive member, which may be the same everywhere, or may vary from one place to the next. A range of about 1 to 100 μm is an example.

(Front Face Wiring pattern and Rear Face Wiring pattern)

The front face wiring patterns are a pair of a first front face wiring pattern and a second front face wiring pattern, a plurality of which are arranged on the front face of the insulator. The pair of the first and second front face wiring patterns are preferably arranged in a regular pattern of columns and rows.

The rear face wiring patterns are a pair of a first rear face wiring pattern and a second rear face wiring pattern, a plurality of which are arranged on the rear face of the insulator. The pair of the first and second rear face wiring patterns are preferably arranged in a regular pattern of columns and rows.

The front face wiring patterns and rear face wiring patterns may each have a pair (first and second), but two or more of the first and/or second front face and/or rear face wiring patterns may be separated within a pair.

(Inner Layer Wiring pattern)

The inner layer wiring pattern has a first inner layer wiring pattern and a second inner layer wiring pattern that are disposed in the interior of the insulator.

The first inner layer wiring pattern is separated from the second front face wiring pattern and the second rear face wiring pattern (that is, these are not electrically connected), and is connected to the first front face wiring pattern and the first rear face wiring pattern. The second inner layer wiring pattern is separated from the first front face wiring pattern and the first rear face wiring pattern, and is connected to the second front face wiring pattern and the second rear face wiring pattern.

The first inner layer wiring pattern extends in a first direction in the interior of the insulator, and the second inner layer wiring pattern has a part that extends in a second direction.

As to the "extends in a first direction" here, as long as the extension direction from one end to the other end of the first inner layer wiring pattern is the first direction, this encompasses not only when the whole first inner layer wiring pattern extends in the first direction, but also when a part of it extends in a different direction from the first direction, and that part may be linked to the part extending in the first direction. The direction that is different form the first direction may be any direction, but examples include a direction that is different from the x axis and y axis directions in two dimensions, and various directions in three directions. It is especially preferable for it to be a three-dimensional direction with respect to the first direction and second direction.

At least one each of the first inner layer wiring pattern and the second inner layer wiring pattern may be provided, but preferably two or more are arranged. In particular, there are preferably a plurality of the first inner layer wiring patterns extending, separated from each other, in the row direction or the column direction. There are preferably a plurality of the second inner layer wiring patterns extending, separated from each other, in the row direction or the column direction. However, they are to be disposed apart from each other so that they do not come into contact.

For example, the first inner layer wiring pattern is preferably such that a wiring pattern extending in the column direction is arranged so as to be separated from a plurality of wiring patterns in the row direction. The second inner layer wiring pattern is preferably such that a plurality of wiring patterns having a part extending in the row direction is arranged so as to be separated from each other in the column direction. However, when the first inner layer wiring patterns and the second inner layer wiring patterns extend in the same planar direction, they preferably extend in a shape (three-dimensional shape) such that one inner layer wiring pattern passes over the other inner layer wiring pattern so that the two do not intersect.

Thus, the first inner layer wiring pattern is configured so that the first inner layer wiring pattern connects (i) the first front face wiring pattern to the corresponding first rear face wiring pattern, (ii) one first front face wiring pattern to other first front face wiring pattern arranged in the first direction, (iii) one first rear face wiring pattern to other first rear face wiring pattern arranged in the first direction, and (iv) the first front face wiring patterns connected each other to the first rear face wiring patterns connected each other.

The second inner layer wiring pattern is configured such that the second inner layer wiring pattern, apart from the first inner layer wiring pattern, connects (i) the second front face wiring pattern to the corresponding second rear face wiring pattern, (ii) one second front face wiring pattern to other second front face wiring pattern arranged in the second direction via the second front face wiring pattern and/or the second rear face wiring pattern, (iii) one second rear face wiring pattern to other second rear face wiring pattern arranged in the second direction are connected via the second front face wiring pattern and/or the second rear face wiring pattern.

(Pads and Heat Dissipation Member)

A plurality of first and second rear face pads are preferably arranged on the rear face of the insulator. For example, these pads are preferably disposed at one or both ends of the rear face wiring patterns arranged in the first direction and the second direction, corresponding to the first inner layer wiring pattern and the second inner layer wiring pattern. That is, first rear face pads are preferably disposed at one or both ends in the first direction with respect to the pair of rear face wiring patterns, and second rear face pads are preferably disposed at one or both ends in the second direction with respect to the pair of rear face wiring patterns. The first rear face pads are preferably connected by the first inner layer wiring patterns to the first rear face wiring patterns, and the second rear face pads are preferably connected by the second inner layer wiring patterns to the second rear face wiring patterns.

There are no particular restrictions on the size of the first and second rear face pads, which can be, for example, from a size corresponding to one rear face wiring pattern to about the size corresponding to the outer shape of the pair of first and second rear face wiring patterns.

The first inner layer wiring patterns and the second inner layer wiring patterns preferably each have wide regions at both ends. These wide regions are preferably disposed at one or both ends of the first inner layer wiring patterns arranged in the first direction, and at one or both ends of the second inner layer wiring patterns arranged in the second direction.

There are no particular restrictions on the size of the wide regions, which can be disposed in a size, position, etc., corresponding to the rear face pads.

Either the first inner layer wiring patterns or the second inner layer wiring patterns may partially branch. In this case, for example, the first inner layer wiring patterns or the second inner layer wiring patterns preferably branch in a region corresponding to the region where a mutually adjacent pair of first and second front face wiring patterns pass over in the column direction or the row direction. Such branching allows branched parts to serve as heat dissipation members, and not as wiring pattern that participates in electrical connection between light emitting elements and the external power supply, and this ensures good heat dissipation in the aggregate board itself. In particular, branching increases the surface area of a material with relatively good heat dissipation properties, such as a conductive member, which ensures better heat dissipation in the aggregate board itself. As a result, when this is used to form a light emitting device, the resulting device will have good heat dissipation and a longer service life.

The insulator may further comprise a third rear face wiring pattern in addition to the pair of first rear face wiring pattern and second rear face wiring pattern. This third rear face wiring pattern can function as a heat dissipation member. In particular, the heat dissipation of the insulator can be further enhanced by connecting this third rear face wiring pattern to the branching part of the inner layer wiring pattern discussed above. The branching part of the inner layer wiring pattern and the third rear face wiring pattern can be connected in the same way as the inner layer wiring pattern and the rear face wiring pattern are connected.

(Layer Structure of Conductive Members)

These conductive members can be constituted by a layer structure. For example, the first front wiring pattern and the second front wiring pattern are preferably constituted by a first conductive layer. The first rear wiring pattern and the second rear wiring pattern are preferably constituted by a eighth conductive layer. The first inner layer wiring pattern is preferably constituted by a second conductive layer that extends in the first direction, a third conductive layer that extends from the second conductive layer toward the first conductive layer, and a fourth conductive layer that extends from the second conductive layer toward the eighth conductive layer. The second inner layer wiring pattern is preferably constituted by a fifth conductive layer that extends in the second direction, a sixth conductive layer that extends from the fifth conductive layer toward the first conductive layer, and a seventh conductive layer that extends from the fifth conductive layer toward the eighth conductive layer.

In particular, it is preferable for the third conductive layer, the fourth conductive layer, the sixth conductive layer, and the seventh conductive layer to extend in the z direction in the above-mentioned three-dimensions. This direction may, however, deviate (incline) by about ±10 degrees.

With this configuration, the conductive members that constitute the pair of positive and negative wiring patterns, etc., can be separated in the aggregate board, so when a plurality of light emitting elements are mounted on the aggregate board, and the electrode pairs of the various light emitting elements are connected to the pair of first and second front face wiring patterns, the various light emitting elements can be lighted while mounted on the aggregate board. As a result, the light emitting elements can be tested for their characteristics individually, allowing for color adjustment and so forth. In particular, when a plurality of first inner layer wiring patterns are separated and/or second inner layer wiring patterns are separated in their disposition, just the light emitting element in a specific location can be tested, and individual characteristics can be tested reliably and easily in today's compact and thin light emitting elements and light emitting devices.

In addition, after the illuminating or other such characteristic testing has been performed, the light emitting element-mounted aggregate board is just split up (discussed below) to complete the light emitting devices that are the final product, which means that light emitting devices can be manufactured more simply.

These conductive layers are preferably formed on/in the above-mentioned insulator layer, for example. When the insulator has a laminate structure of two or more layers, for instance, the insulator is preferably such that the first conductive layer, the second conductive layer, the fifth conductive layer and the eighth conductive layer are disposed on its front face or rear face, and the third conductive layer, the fourth conductive layer, the sixth conductive layer and the seventh conductive layer are provided in its interior.

The insulator preferably has at least one layer, for example, (1) disposed the first conductive layer on its front face or rear face, (2) disposed the second conductive layer on its front face or rear face, (3) disposed the fifth conductive layer on its front face or rear face, (4) disposed the second conductive layer and the fifth conductive layer on its (5) disposed the first conductive layer on its front face or rear face, and disposed the second conductive layer on its rear face or front face, (6) disposed the first conductive layer on its front face or rear face, and disposed the fifth conductive layer on its rear face or front face, (7) disposed the first conductive layer on its front face or rear face, and disposed the second conductive layer and the fifth conductive layer on its rear face or front face, (8) disposed the eighth conductive layer on its front face or rear face, (9) disposed the eighth conductive layer on its front face or rear face, and disposed the second conductive layer on its rear face or front face,

(10) disposed the eighth conductive layer on its front face or rear face, and disposed the fifth conductive layer on its rear face or front face,

(11) disposed the eighth conductive layer on its front face or rear face, and disposed the second conductive layer and the fifth conductive layer on its rear face or front face,

(12) disposed the second conductive layer on its front face or rear face, and disposed the fifth conductive layer on its rear face or front face.

The layers of (1) to (12) may be met at least one layer, for example,

(13) provided the third conductive layer in its interior,
(14) provided the sixth conductive layer in its interior,
(15) provided the third conductive layer and the sixth conductive layer in its interior,
(16) provided the fourth conductive layer in its interior,
(17) provided the seventh conductive layer in its interior,
(18) provided the fourth conductive layer and the seventh conductive layer in its interior,
(19) provided the third conductive layer and the seventh conductive layer in its interior,
(20) provided the fourth conductive layer and the sixth conductive layer in its interior.

When the insulator has a laminate structure of two layers, for instance, the insulator preferably has the layer of the above (1), (4), (7), (15) or (18), more preferably has the layers of the above (1) and (4) all together, and still preferably has the layers of the above (1), (4) and (15) all together. Alternatively, the insulator preferably has the layer of the above (8), more preferably has the layers of the above (8) and (4) or the above (8) and (18) all together, still preferably has the layers of the above (1) and (8) all together, and further still preferably has the layers of the above (8) and (18) or the above (1), (8) and (18) all together. Of these, the insulator is preferred of two layers laminate structure having the layers of the above (1) and (15) all together, or the layers of the above (8) and (18) all together. The insulator of two layers laminate structure more preferably meets the above (7) or (11).

For example, the second conductive layer and the fifth conductive layer may be formed on another face, namely, either a layer having the first conductive layer on one side or a layer having the eighth conductive layer on one side. That is, the second conductive layer and the fifth conductive layer may be formed on another face, namely, either a layer having the first conductive layer on one side or a layer having the eighth conductive layer on one side.

The second conductive layer and fifth conductive layer, the third conductive layer and the sixth conductive layer, and the fourth conductive layer and the seventh conductive layer may not be formed by layers obtained in the same film formation step, respectively, but they are preferably formed by the same layer, respectively.

When the insulator has a laminate structure of three layers, for instance, the insulator preferably has the layer of the above (1), (2), (3) or (8), or the layer of the above (13), (14) or (15), or the layer of the above (16), (17) or (18), more preferably has the layers of the above (1) and (2) all together, or the layers of the above (1) and (3) all together, or the layers of the above (8) and (2) all together, or the layers of the above (8) and (3) all together, and still more preferably has the layers of the above (1), (2) and (15) all together, or the layers of the above (1), (3) and (15) all together, or the layers of the above (8), (2) and (18) all together, or the layers of the above (8), (3) and (18) all together, and further still preferably has the layers of the above (1), (8) (15) and (18) all together, Of these, the insulator of three layer laminated structure preferably has the layers of the above (5) and (15) all together, or the layers of the above (12) and (15) all together, or the layers of the above (10) and (18) all together, or the layers of the above (6) and (15) all together, or the layers of the above (12) and (19) all together, or the layers of the above (11) and (18) all together. In particular, the insulator having the layers of the above (1), (8), (15), (18) and (20) all together, or the layers of the above (1), (8), (15), (18) and (19) all together is preferred. However, the second conductive layer may be formed on another face, namely, a layer having the first conductive layer on one side, or a layer having the eighth conductive layer on one side, or a layer having the fifth conductive layer on one side. Alternatively, the fifth conductive layer may be formed on another face, namely, either a layer having the first conductive layer on one side, a layer having the eighth conductive layer on one side, or a layer having the second conductive layer on one side.

All or part of the third conductive layer and the sixth conductive layer, and/or the fourth conductive layer and the seventh conductive layer, may be formed by the same layer, or may be formed by different layers.

An aggregate board having the above configuration has a simple wiring pattern structure corresponding to an xyz three-dimensional structure, and can therefore be manufactured easily, without going through any special steps, and the aggregate board can be in the form of a thin-film.

[Light Emitting Device]

The light emitting device is configured such that a plurality of light emitting elements are mounted on a pair of first and second front face wiring patterns (hereinafter also referred to as front face wiring patterns) of the above-mentioned aggregate board, electrodes of pairs of each of the light emitting elements are connected via joining members to the pairs of first and second front face wiring patterns, and the resulting product is divided into individual light emitting elements or into groups of light emitting elements.

Therefore, a single light emitting device includes a board produced by dividing an aggregate board, and a light emitting element mounted on the front face of this board, and further includes a joining member that connects the light emitting element to the substrate front face. The light emitting device preferably further includes a fluorescent material layer that covers the light emitting element, and more preferably further includes a reflective layer disposed around the light emitting element.

The board here is preferably one in which the above-mentioned insulator has the first inner layer wiring pattern exposed at two places at its ends, and has the second inner layer wiring pattern exposed at two places. Since a light emitting device is usually square in plan view shape, it is preferable that the first inner layer wiring pattern is exposed at a pair of end faces including two opposing edges, and the second inner layer wiring pattern is exposed at a pair of end faces including the other two opposing edges.

Also, the first inner layer wiring pattern and the second inner layer wiring pattern may be exposed at the end faces of the insulator at the same or different locations in the thickness direction of the insulator.

Either the first inner layer wiring pattern or the second inner layer wiring pattern may be partially branched. In this case, for example, the first inner layer wiring pattern or the second inner layer wiring pattern is preferably branched in a region corresponding to the region passing over the pair of first and second rear face wiring patterns that are mutually adjacent in the column direction or the row direction. This branching, as discussed below, allows the branched part to be wiring pattern that does not contribute to electrical connection between the light emitting element and the external power supply, and ensures good heat dissipation in the aggregate board itself. In particular, even better heat dissipation can be ensured in the aggregate board itself by increasing the surface area of a material with relatively good heat dissipation properties, such as the conductive members. As a result, when this is used to form a light emitting device, the resulting light emitting device will have good heat dissipation and a longer service life.

Also, the insulator (board) may include on its rear face a third rear face wiring pattern in addition to the first rear face wiring pattern or the second rear face wiring pattern. This third rear face wiring pattern can function as a heat dissipation member. In particular, connecting this third rear face wiring pattern to the above-mentioned branched part of the inner layer wiring pattern will improve the heat dissipation of the insulator even more. The "branched part of the inner layer wiring pattern" here refers to a third inner layer wiring pattern. This third inner layer wiring pattern is preferably exposed near the exposed part of the second inner layer wiring pattern at the end face of the board, such as at the same location in the thickness direction of the insulator. This increases the contact surface area with the outside, and further contributes to better heat dissipation.

With this configuration, as discussed above, electrical conduction can be achieved without short-circuiting the individual light emitting elements in a state in which the light emitting elements are mounted on the aggregate board, so the individual light emitting elements can be lighted. This allows the characteristics to be testing, and an adjustment step can be individually added for light emitting elements that are giving off the wrong color, etc. As a result, the characteristics of the resulting light emitting device can be maintained at a high quality level, and the yield of light emitting devices obtained from a single aggregate board can be raised.

(Light Emitting Element)

A light emitting diode is preferably used as the light emitting element. Example thereof includes a laminated structure including a light emitting layer made of a nitride semiconductor such as InN AlN, GaN, InGaN, AlGaN, InGaAlN, a III-V compound semiconductor, a II-V compound semiconductor and other various semiconductor layers formed on the substrate. Examples of the substrate include an insulating substrate such as sapphire ($Al_2O_3$), and an conductive substrate such as SiC, GaN, GaAs. The light emitting element may not eventually include the substrate.

When the board of the light emitting elements has insulating properties, a conductive layer may be temporarily necessary on the front face of the board in order to form the fluorescent material layer by electrodeposition or the like (discussed below). This conductive layer may be removed prior to the step of forming the reflective layer (discussed below), but insulating properties are preferably imparted by oxidation or the like. This forms a translucent layer having good adhesion to the fluorescent material layer (discussed below). When oxidation is used, it is preferable if the oxidation modifies the layer to be translucent, or if the layer can be modified into a member that is highly translucent. Examples of the conductive layer and/or the translucent layer include Mg, Al, Si, Zr, An and Pb.

When the board of the light emitting elements is conductive, in order to prevent the reflective layer from being formed on the light emitting element, so after the fluorescent material layer (discussed below) has been formed, a cover film may be formed from a material that is translucent and insulating over the fluorescent material layer formed over the light emitting elements. The cover film may be formed of an oxide such as $Al_xO_y$ ($1<x, 1<y$), $SiO_x$ ($1<x$), and an organic substance such as polymethylmethacrylate, polyimide, silicone resin.

Joining Member

The joining member is used to mount the light emitting elements on the board. The light emitting elements may be mounted face-up on the board, but flip-chip mounting is preferable. The joining member is disposed so as to be interposed between at least the front face wiring pattern and the electrodes of the light emitting elements in order to join the light emitting elements to the front face wiring pattern of the board, for example. A material that affords electrical conduction between the light emitting elements and the front face wiring pattern is used as the joining member. Examples of the junction member include, for example, a solder such as Sn—Bi, Sn—Cu, Au—Sn, a conductive past such as Ag, Au, Pd, a bump, a anisotropic conductive material, a low-melting-point metal and other brazing filler metal.

Fluorescent Material Layer

The fluorescent material layer converts light from the light emitting elements into a different wavelength. For instance, the fluorescent material layer may be one that converts light from the light emitting elements into a shorter wavelength, but one that converts to a longer wavelength is preferable from the standpoint of light extraction efficiency. The fluorescent material layer is disposed at least on the front face of the front face wiring pattern exposed around the region where the light emitting elements are disposed on the upper face of the board, and the upper and side faces of the light emitting elements. Covering the upper and side faces of the light emitting elements with the fluorescent material layer allows the light emitted upward and laterally from the light emitting elements to be extracted first on the fluorescent material layer side, and this reduces absorption of light within the light emitting elements.

Examples of the fluorescent material forming the fluorescent material layer include a fluoride complex fluorescent material activated by manganese ($A_2MF_6$: Mn (A represents at least one selected from Li, Na, K, Rb, Cs, $NH_4$; M represents at least one selected from Ge, Si, Sn, Ti, Zr), for example, $K_2SiF_6$:Mn(KSF), KSNAF($K_2Si_{1-x}Na_xAl_xF_6$:Mn), $K_2TiF_6$:Mn(KTF), etc.); a nitride or oxynitride fluorescent material activated by a lanthanoid element such as Eu, Ce, for example, α- or β-sialon fluorescent material or an alkali earth metal nitride silicate fluorescent material activated by a lanthanoid element such as europium; an alkali earth metal halogen apatite, an alkali earth halosilicate, alkali earth metalsilicate, alkali earth metal halogen borate, alkali earth metal aluminate, alkali earth metal silicate, alkali earth metal sulfide, alkali earth metal thiogallate, alkali earth metal silicone nitride or germinate fluorescent material activated by a lanthanoid element such as europium or a transition metal such as manganese; a rare earth aluminate or rare earth silicate fluorescent material activated by a lanthanoid element such as cerium; an organic or organic complex fluorescent material activated by a lanthanoid element such as europium, and the like.

There are no particular restrictions on the shape of the fluorescent material, but spherical or close to that shape is preferable, for example, and it is more preferable that the average particle size is about 1 to 100 μm, and still more preferable of 1 to 10 μm.

The fluorescent material layer is usually formed at a part that includes the upper faces of the light emitting elements and the front face wiring pattern exposed around the light emitting elements (that is, the front faces of the first front face wiring pattern and the second front face wiring pattern), after the light emitting elements have been mounted on the board.

The fluorescent material layer can be formed by electrodeposition, electrostatic coating, sputtering, vapor deposition, potting, printing, spraying, or another such method. Sputtering, vapor deposition, and sedimentation allow the fluorescent material layer to be affixed to the entire board and light emitting elements without the use of a binder. Potting, printing, and spraying allow the fluorescent material to be applied selectively, by using a fluorescent material that is dispersed in a translucent member. The translucent member here can be formed from a material capable of transmitting at least 60%, and preferably at least 70%, and more preferably at least 80% of the peak wavelength of the light emitting elements, and can be suitably selected from among the thermosetting resins and thermoplastic resins discussed below.

It is especially favorable for the fluorescent material layer to be formed by electrodeposition or electrostatic coating.

Electrodeposition and electrostatic coating allow the fluorescent material to be selectively applied to the area where the fluorescent material layer is to be formed, by disposing a conductive material in that area. These methods allow a fluorescent material layer of a uniform thickness to be formed at the desired location.

With electrodeposition, the fluorescent material layer is applied, for example, by placing the board on which the light emitting elements have been mounted in a solution containing the fluorescent material (electrodeposition solution). Then, by electrophoresis in the solution, the fluorescent material particles are deposited on the surface of the light emitting elements and the front face wiring pattern of the board.

With electrostatic coating, the fluorescent material is added to a vapor phase, a board is placed in this vapor, and the fluorescent material particles are deposited on the surface of the light emitting elements and on the front face wiring pattern of the board to form a fluorescent material layer.

When the surface of the light emitting elements is made from a conductive material, then charged fluorescent material particles can be deposited by electrophoresis on the light emitting elements by applying voltage to the light emitting elements themselves.

When the surface of the light emitting elements has a non-conductive part, as with light emitting elements produced by depositing a semiconductor on sapphire or another such insulating board, a conductive layer is provided to the non-conductive part of the light emitting elements, and then voltage is applied to this conductive layer, which deposits charged fluorescent material particles by electrophoresis via the conductive layer.

The thickness of the fluorescent material layer may vary depending on where the layer is disposed. For instance, the thickness of a fluorescent material layer disposed on the first front face wiring pattern may be different from the thickness of the fluorescent material layer disposed on the second front face wiring pattern.

With an aggregate board having the wiring pattern structure discussed above, it is possible to apply different potentials to the first front face wiring pattern and the second front face wiring pattern. This makes it possible to form fluorescent material layers of different thicknesses at the first front face wiring pattern and the second front face wiring pattern. In particular, if a higher positive potential is given to one front face wiring pattern than the other, no fluorescent material layer will be formed on the front face wiring pattern to which the higher positive potential was given. In other words, it is possible to form the fluorescent material layer on just one of the first and second front face wiring patterns.

Figure 5A:
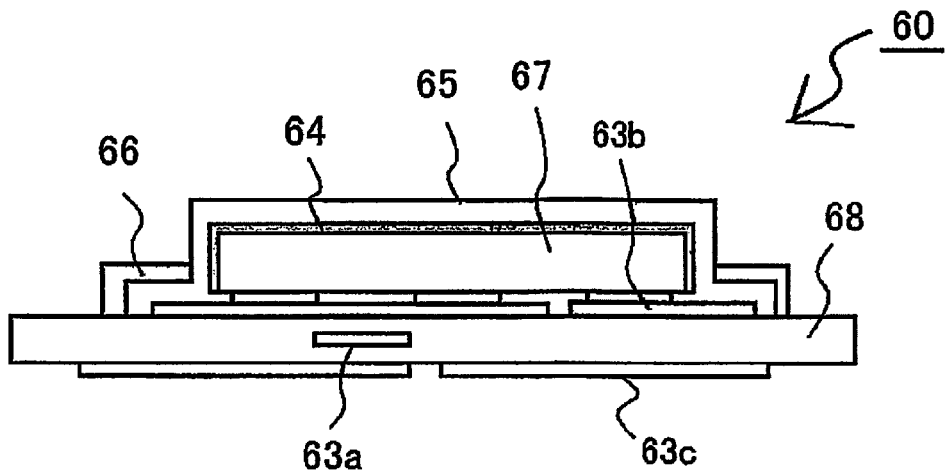
FIG. 5A is a simplified cross section of an example of the light emitting device of the present disclosure.
Figure 5B:
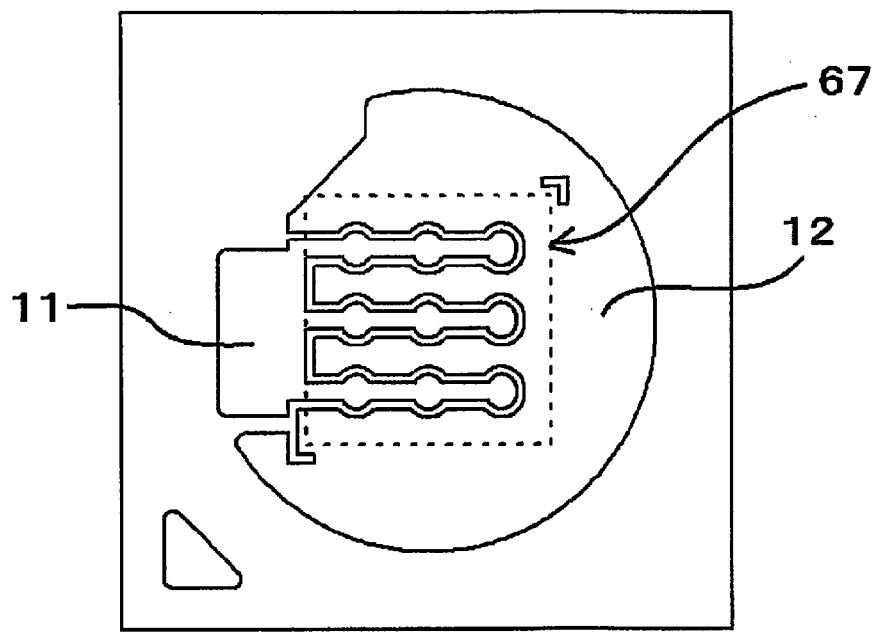
FIG. 5B is a simplified plan view of the positional relation between the board and the light emitting elements in the light emitting device of the present disclosure.

As shown in FIG. 5B, for example, the fluorescent material can be made less likely to adhere to the front face wiring pattern near a light emitting element 67, which is square in top view, by positioning one front face wiring pattern (here, a second front face wiring pattern 12) near three of the four sides of the light emitting element 67.

A large quantity of fluorescent material will be necessary when the light emitting device emits light with a low color temperature, such as with warm colors. Accordingly, with a method for forming a fluorescent material by electrostatic coating, the coating will sometimes be so thick that the upper face of the fluorescent material layer formed on front face wiring pattern near a light emitting element will be formed up to a level that is close to the upper face of the light emitting element. However, it is preferable to cover just the light emitting element with the fluorescent material layer in order to obtain a light emitting device with little color unevenness, as with a point light source, and it is preferable to form no fluorescent material layer at all, or to form it as thin as possible, over the front face wiring pattern around the light emitting element. With a wiring pattern structure such as that discussed above, a coating can be applied that imparts conductive only to locations corresponding to a light emitting element or wiring pattern in a specific location. This effectively prevents the fluorescent material layer from adhering in regions where it is not needed.

The thickness of the fluorescent material layer can be suitably adjusted by varying the fluorescent material particle deposition conditions and duration. The fluorescent material layer that covers the light emitting element is preferably formed in a substantially uniform thickness. The fluorescent material layer preferably has a thickness of about 0.01 to 100 µm.

The conductive layer is either removed or modified to be insulating before the reflective layer is formed. For instance, this can be accomplished by (1) after forming the conductive layer, adding a material that will selectively dissolve the material of the conductive layer to the electrodeposition solution, (2) after forming the fluorescent material layer, dipping the conductive layer in a solution to dissolve, (3) after forming the fluorescent material layer, modifying the conductive layer to be insulating by oxidation or other such processing, or another such method. With methods (1) and (2) above, the conductive layer is dissolved by being dipped in hydrochloric acid, sulfuric acid, or another such acidic solution, or in sodium hydroxide, ammonia, or another such alkaline solution. Aluminum, zinc, or the like can be used for the material of the conductive layer here. With method (3) above, in addition to modification to being insulating, it is preferable to modify to a member that is highly translucent, or modify to being translucent. Examples of the material of this conductive layer include magnesium, aluminum, silicon, zirconium, and lead. The thickness of the conductive layer should be adequate to allow the above-mentioned processing, and can be from 10 to 1000 nm, for example.

When the light emitting element board is conductive, after the fluorescent material layer is formed, a cover film may be formed from a material that is translucent and insulating over the fluorescent material layer formed on the light emitting element in order to prevent the reflective layer from being formed on the light emitting element. Examples of the material for a cover film includes an oxide such as $Al_xO_y$ ($1<x$, $1<y$), $SiO_x$ ($1<x$), an organic substance such as polymethyl methacrylate, polyimide or silicone resin.

Reflective Layer

The reflective layer covers the fluorescent material layer formed on the first and second front face wiring patterns, and serves to minimize the decrease in light extraction efficiency.

The reflective material that makes up the reflective layer is preferably one that can efficiently reflect light emitted from the light emitting element and light whose wavelength has been converted by the fluorescent material layer, and more preferably one that can reflect at least 80%, and even more preferably at least 90%, of the peak wavelength thereof.

The reflective layer is preferably made from a material that transmits, and tends not to absorb, the light emitting element and light whose wavelength has been converted by the fluorescent material layer. The material is also preferably insulating.

There are no particular restrictions on the reflective material, but light can be reflected more efficiently by using a material that can reflect light, such as a powder of $SiO_2$, $TiO_2$, $ZrO_2$, $BaSO_4$, MgO, or the like. These materials may be used singly or in combinations of two or more types. These material is preferably used by mixing the resin. Examples of the resin include a thermosetting resin and a thermoplastic resin. Specific Examples of such a resin include an epoxy resin; a silicone resin; a modified epoxy resin such as a silicone modified epoxy resin; a modified silicone resin such as an epoxy modified silicone resin; a hybrid silicone resin, a polyimide resin, a modified polyimide resin, polyphthalamide (PPA), a polycarbonate resin; a polyphenylene sulfide (PPS); a liquid crystal polymer (LCP); an ABS resin (an acrylonitrile-butadiene-styrene resin); a phenolic resin; an acrylic resin; and a PBT resin (polybutylene terephthalate resin).

As discussed above, when the fluorescent material layer is formed by electrodeposition, etc., fluorescent material particles will adhere to the conductive parts exposed on the surface of the light emitting device (that is, that are in contact with the electrodeposition solution), such as the surface of the front face wiring pattern exposed around the light emitting element. In contrast, the reflective layer is formed so as to cover the fluorescent material layer formed on the front face wiring pattern exposed around the light emitting element. Consequently, the light emitted from the fluorescent material disposed on the surface of the light emitting element can reduce the loss of light caused by absorption in the fluorescent material layer provided on the front face wiring pattern around the light emitting element. Also, light emitted from the fluorescent material layer formed on the front face wiring pattern can be blocked by the reflective layer, and the light emitting device can be moved closer to being a point light source.

Also, when the fluorescent material layer is formed by electrodeposition, etc., the fluorescent material particles may not be able to sufficiently cover a portion of the gap provided between the lower face of the semiconductor layer and the upper face of the board. The reflective layer can cover all the way around this gap when the reflective layer is formed over the fluorescent material layer provided on the front face wiring pattern. As a result, this prevents light from the light emitting element from leaking out through the above-mentioned gap.

The reflective layer preferably covers the entire surface of the fluorescent material layer formed on the front face wiring pattern. This allows the above-mentioned effect to be manifested more efficiently.

The reflective layer preferably has a thickness of about 1 to 100 μm, for example. It is particularly favorable for the reflective layer to be formed so that the upper face of the reflective layer is disposed above the lower face of the semiconductor layer of the light emitting element. This prevents light from the light emitting element from leaking out through the above-mentioned gap. Also, the relatively strong light emitted from the side faces of the semiconductor layer, including the light emitting layer, can be blocked by the reflective layer, and there will be less color unevenness.

The upper face of the reflective layer is preferably disposed below the upper face of the light emitting element. This allows light emitted in the side face direction of the light emitting element to be taken off to the outside without being blocked by the reflective layer. Also, the relatively strong light emitted from the side faces of the light emitting layer can be taken off to the outside via the fluorescent material layer. Furthermore, there will be less absorption of light by the front face wiring pattern around the light emitting element and by the fluorescent material layer provided over it.

To dispose the reflective layer below the upper face of the light emitting element, the fluorescent material layer formed on the front face wiring pattern is preferably as thin as possible. As discussed above, even when a large quantity of fluorescent material is required, the fluorescent material layer on the front face wiring pattern can still be made thinner.

Method for Testing Light Emitting Element

First, a plurality of light emitting elements are connected to the pairs of first and second front face wiring patterns on the aggregate board.

After this, the light emitting elements are lighted to test the characteristics of each light emitting element.

The characteristics of the light emitting element referred to here means that a light emitting element can be lighted by applying positive and negative voltage to the pairs of first and second front face wiring patterns or the pairs of first and second rear face wiring patterns. Thus, various light emitting element characteristics can be tested, including whether or not an element will light.

In particular, if the aggregate board comprises a plurality of pairs of first and second front face wiring patterns arranged regularly in the column and row directions, and comprises a plurality of first inner layer wiring patterns that are separated from each other in the column direction or the row direction, and further comprises a plurality of second inner layer wiring patterns that are separated from each other in the column direction or the row direction, then the light emitting elements can be lighted in units of just one, a column, a row, or any specific number, so more detailed characteristics can be tested for, such as luminance, brightness, and color.

For example, if the fluorescent material layer that covers the light emitting elements is formed after the light emitting elements have been mounted on the aggregate board, the color of light produced by the fluorescent material layer can be measured by illuminating each light emitting element. Accordingly, when this color measurement (individual color testing) reveals insufficient formation of the fluorescent material layer, a step can be executed to add another fluorescent material layer to just certain light emitting elements. This allows all of the light emitting elements to be adjusted to the proper color, which increases the yield.

Any of the fluorescent material layer manufacturing methods discussed above may be used to form the fluorescent material layer, but it is preferably formed by electrodeposition or electrostatic coating because this allows the layer to be formed accurately and easily at the desired locations. In this case, the fluorescent material layer may be formed on the first and second front face wiring pattern surfaces around the light emitting elements, but also may be formed on the first and second front face wiring pattern surfaces around the light emitting elements and on just one surface or just one of the plurality of light emitting elements. In the latter case, light emitting devices that have different fluorescent material layers can be obtained on a single aggregate board.

Any of the above-mentioned fluorescent material layer manufacturing methods may be used to add another fluorescent material layer, but this is preferably accomplished by jet dispenser coating with a solution containing a fluorescent material. This is because a fluorescent material layer can be added very easily to a single light emitting element.

The thickness of the additional fluorescent material layer is from 5 to 100 μm, for example.

Figure 7A:
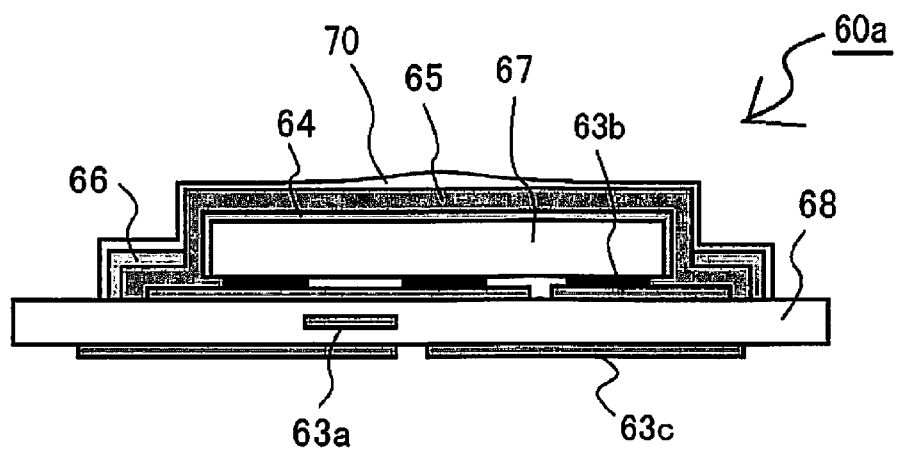
FIG. 7A is a simplified cross section of an example of the light emitting device of the present disclosure.
Figure 7B:
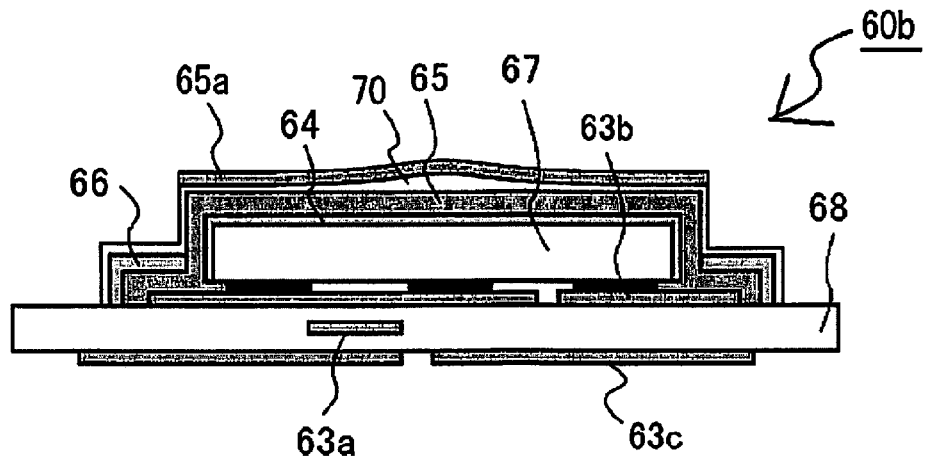
FIG. 7B is a simplified cross section of an example of the light emitting device of the present disclosure.

As shown in FIG. 7B, for example, a translucent resin layer (70 in FIG. 7B) may be formed on the fluorescent material layer 65 and/or the reflective layer 66 (discussed below) prior to the jet dispenser coating. In this case, the fluorescent material layer, the translucent resin layer, and the additional fluorescent material layer are laminated in that order on the upper face of the light emitting element. Thus forming a translucent resin layer increases the adhesion of the fluorescent material layer and reflective layer. In particular, when the fluorescent material layer or the reflective layer becomes brittle to the high air pressure resulting from the jet dispenser, such as when these layers are formed by electrodeposition, etc., deformation and separation of these layers can be effectively avoided. When the above-mentioned fluorescent material layer or reflective layer is resistant to air pressure, etc., the translucent resin layer need not be provided. In this case, there is one less resin layer interface above the light emitting elements as compared to when a translucent resin layer is provided, so this is advantageous in terms of light extraction efficiency.

As shown in FIG. 7B, the translucent resin layer 70 may cover all of the fluorescent material layer 65 or the reflective layer 66, or may cover only a part. Also, as shown in FIG. 7A, an additional fluorescent material layer 65a does not necessarily need to be formed, and just the translucent resin layer 70 may be formed to protect the fluorescent material layer 65 and the reflective layer 66.

As shown in FIGS. 7A and 7B, the additional fluorescent material layer and the optionally formed translucent resin layer are preferably formed so that their upper faces protrude. This reduces the proportion of light from the light emitting elements that is totally reflected by the surface of the additional fluorescent material layer or the translucent resin layer, and increases the light extraction efficiency.

Also, the upper faces may be flat in another mode of the additional fluorescent material layer and the optionally formed translucent resin layer. In this case, the thickness can be reduced in the height direction of the additional fluorescent material layer or the translucent resin layer that cover the light emitting elements, so light emitting devices with less of a decrease in luminance can be obtained.

The translucent resin layer can be formed from the resin such as a thermosetting resin and a thermoplastic resin. The "translucent" means that it allows penetration of light, which is 60% or greater of light emitted from the light emitting layer, and further preferably allows penetration of 70% or greater, 80% or greater, or 90% or greater of light emitted from the light emitting layer.

The translucent resin layer can be formed by potting, printing, spraying, or another such method.

When the translucent resin layer is formed, its thickness is from 5 to 100 μm, for example. The translucent resin layer is preferably thinner than the additional fluorescent material layer.

Also, a reflective layer may be further formed around the light emitting elements before or after testing the characteristics of the light emitting elements, following the formation of the fluorescent material layer. The reflective layer here is preferably formed by electrodeposition or electrostatic coating over the fluorescent material layer on the first and second front face wiring pattern surfaces around the light emitting elements, and on the surface of the light emitting elements. This limits the reflection of light, so light whose wavelength has been converted by the fluorescent material layer and light emitted from the light emitting elements can be adjusted more closely to the desired color.

An embodiment of the aggregate board, light emitting device, and light emitting element testing method of the present disclosure will now be described in specific terms through reference to the drawings.

Embodiment 1

Aggregate Board

As shown in FIG. 1A, the aggregate board 10 in this embodiment comprises an insulator 9 composed of an alumina ceramic, and front face wiring patterns, rear face wiring patterns, and inner layer wiring patterns made of gold. The aggregate board 10 has pairs of each wiring pattern disposed within a mounting region 9a of one light emitting element, and a plurality of these units are arranged in columns and rows (such as 3×3).

As shown in FIGS. 1A to 1F, the insulator 9 has a two-layer structure consisting of an upper layer A and a lower layer B.

A front face wiring pattern is disposed on the front face Aa of the upper layer A of the insulator 9. The front face wiring pattern comprises pairs of first front face wiring pattern 11 and second front face wiring pattern 12 arranged in a matrix. The first front face wiring patterns 11 and the second front face wiring patterns 12 are constituted by a first conductive layer 1.

A rear face wiring pattern is disposed on the rear face Bb of the lower layer B of the insulator 9. The rear face wiring pattern comprises pairs of first rear face wiring pattern 21 and second rear face wiring pattern 22 arranged in a matrix and corresponding to the first front face wiring patterns 11 and the second front face wiring patterns 12. The first rear face wiring patterns 21 and the second rear face wiring patterns 22 are constituted by an eighth conductive layer 8.

First inner layer wiring patterns 31 and second inner layer wiring patterns 32 are arranged between the front faces Aa of the upper layer A of the insulator 9 and the rear faces Bf of the lower layer B.

The first inner layer wiring patterns 31 are made up, for example, of a second conductive layer 2 that extends in the column direction, a third conductive layer 3 that extends from this second conductive layer 2 toward the first conductive layer 1, and a fourth conductive layer 4 that extends from the second conductive layer 2 toward the eighth conductive layer 8. With this configuration, the first inner layer wiring patterns 31 are connected to the first front face wiring patterns 11 and the first rear face wiring patterns 21, and are separated from the second front face wiring patterns 12 and the second rear face wiring patterns 22. Of the first inner layer wiring patterns 31, the second conductive layer 2, for example, extends in three mutually separated lines in the column direction (the first direction; x in FIG. 1A).

The second inner layer wiring patterns 32 are made up, for example, of a fifth conductive layer 5 that extends in the row direction (the second direction; y in FIG. 1A), a sixth conductive layer 6 that extends from this fifth conductive layer 5 toward the first conductive layer 1, and a seventh conductive layer 7 that extends from the fifth conductive layer 5 toward the eighth conductive layer 8. This configuration is connected to the second front face wiring patterns 12 and the second rear face wiring patterns 22 via the second front face wiring patterns 12 and/or the second rear face wiring patterns 22, and is separated from the first front face wiring patterns 11 and the first rear face wiring patterns 21. Of the second inner layer wiring patterns 32, the fifth conductive layer 5, such as wiring pattern having a part extending in the row direction, extends, for example in three mutually separated lines. The fifth conductive layer 5 is segmented so as to partially avoid the second conductive layer 2 at the front face Ba of the lower layer B, so as not to intersect or touch the conductive layers constituting the first inner layer wiring patterns 31.

The second conductive layer 2 and the fifth conductive layer 5, for example, are disposed as layers formed in the same film formation step, on the front face Ba of the lower layer B.

The third conductive layer 3 and the sixth conductive layer 6 are disposed as layers formed in the same film formation step, so as to embed through-holes, in the interior of the upper layer A.

The fourth conductive layer 4 and the seventh conductive layer 7 are disposed as layers formed in the same film formation step, so as to embed through-holes, in the interior of the lower layer B.

As shown in FIGS. 1C to 1F, for example, the positions where the third conductive layer 3 and the sixth conductive layer 6 come into contact with the first conductive layer 1, the second conductive layer 2 and the fifth conductive layer 5, and the positions where the fourth conductive layer 4 and the seventh conductive layer 7 come into contact with the second conductive layer 2, the fifth conductive layer 5 and the eight conductive layer 8 are set so as to connect at the shortest distance, at one or more places within the mounting region 9a of a single light emitting element. However, the first conductive layer 1 constituting the second front face wiring patterns 12, and the fifth conductive layer 5 constituting the second inner layer wiring patterns 32 are connected at one place each on both sides of the second conductive layer 2 constituting the first inner layer wiring patterns 31 within the mounting region 9a of a single light emitting element.

The rear face Bb of the lower layer B of the insulator 9 has rear face pads in the region where the paired first rear face wiring patterns 21 and second rear face wiring patterns 22 are arranged, that is, around the outside of the region corresponding to the mounting region 9a of a single light emitting element.

The rear face pads are such that first rear face pads 21a are arranged in two rows, corresponding to the number of regions, in the row direction of the regions, and second rear face pads 22a are arranged in two rows, corresponding to the number of regions, in the column direction of the regions. The first rear face pads 21a are connected to the first rear face wiring patterns 21 by the first inner layer wiring patterns 31, while the second rear face pads 22a are connected to the second rear face wiring patterns 22 by the second inner layer wiring patterns 32.

The second conductive layer 2 and the fifth conductive layer 5 are wider on both sides around the outside of the mounting region 9a of a single light emitting element, that is, at locations corresponding to rear face pads. These wider regions 31a and 32a are disposed in a number corresponding to the rear face pads. These wider regions 31a and 32a are connected to the rear face pads by the fourth conductive layer 4 and the seventh conductive layer 7.

Figure 1C:
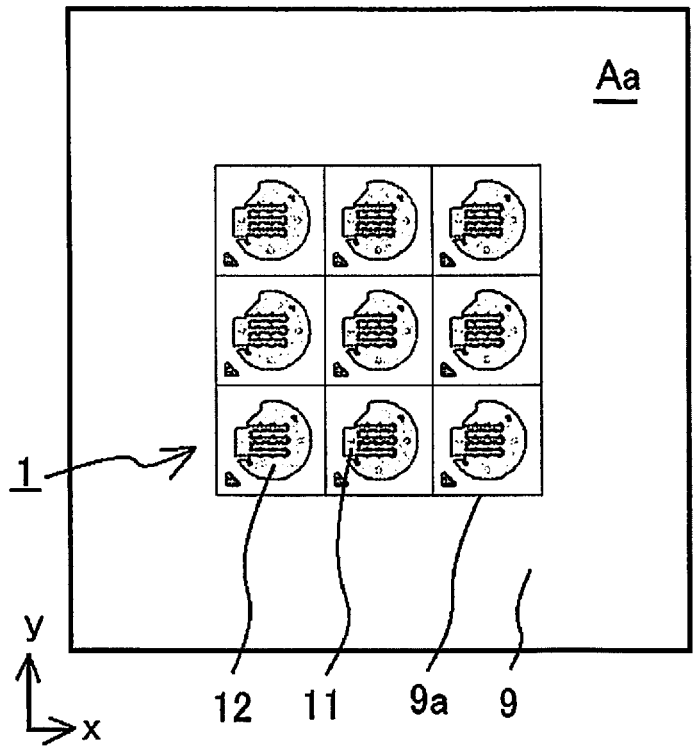
FIG. 1C is a plan view of the front face of the aggregate board in FIG. 1A.
Figure 1D:
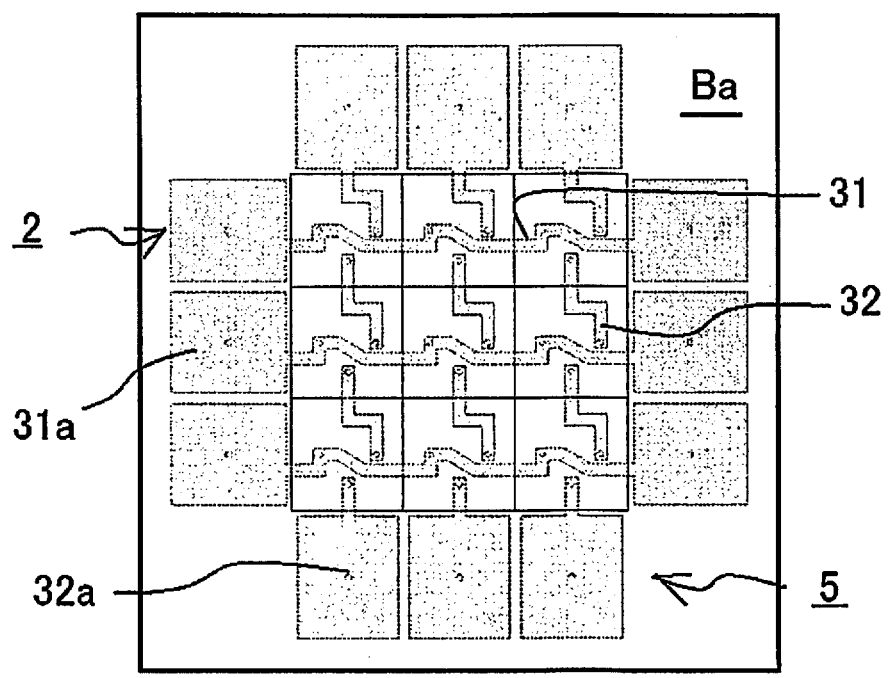
FIG. 1D is a plan view of the inner layer wiring pattern of the aggregate board.
Figure 1E:
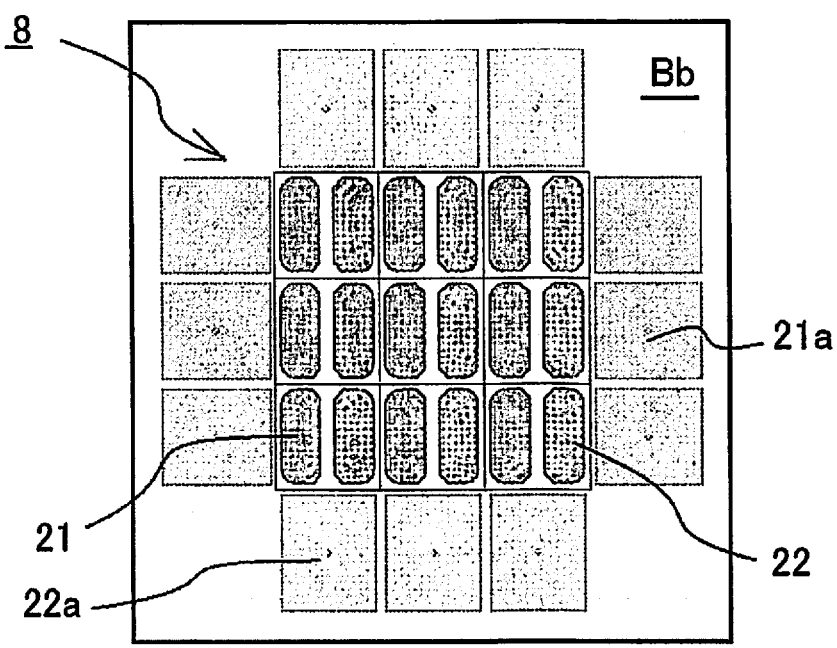
FIG. 1E is a plan view of the rear face of the aggregate board.
Figure 1F:
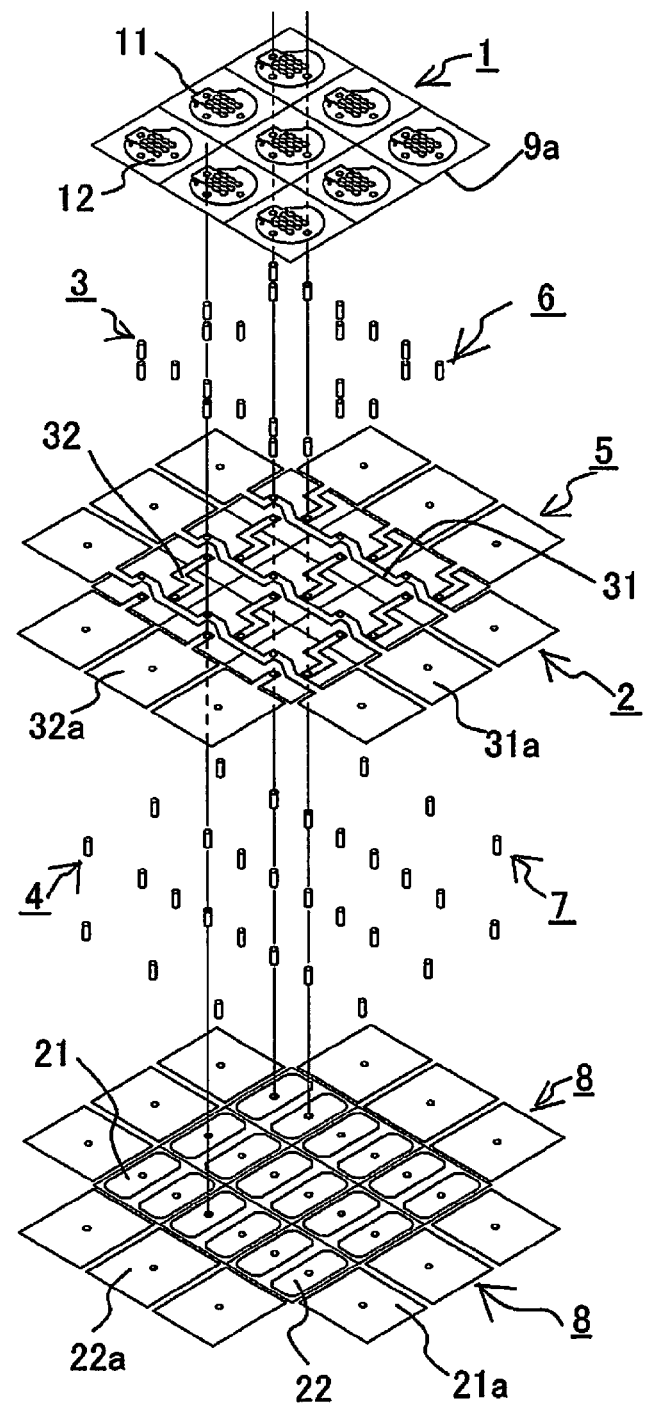
FIG. 1F is a simplified oblique view of just the conductive member (thickness not shown) in the aggregate board.
Figure 1G:
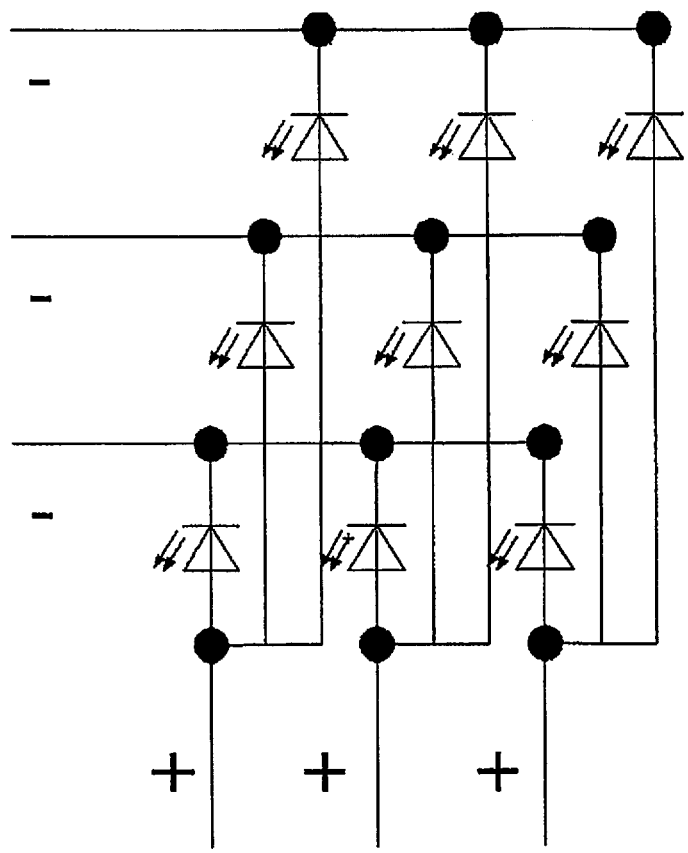
FIG. 1G is an electrical wiring pattern diagram of the aggregate board.

As shown in FIG. 1G, the aggregate board thus configured features an extremely simple light emitting element mounting board, and positive and negative power supplies can be applied in column and row units without short-circuiting the positive and negative wiring patterns.

Embodiment 2

Aggregate Board

Figure 2A:
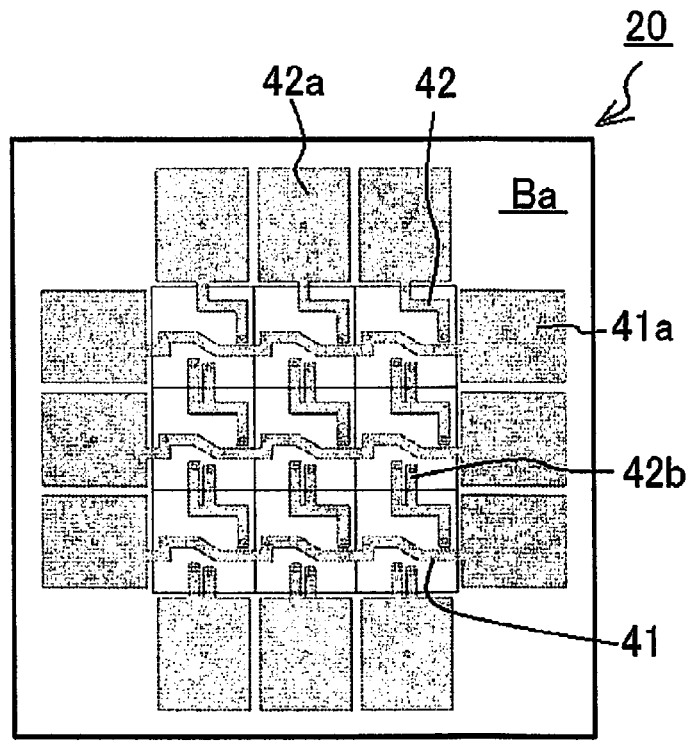
FIG. 2A is a plan view of the inner layer wiring pattern of the aggregate board.

As shown in FIG. 2A, the aggregate board 20 in this embodiment is configured substantially the same as the aggregate board 10 in Embodiment 1, except that the inner layer wiring pattern is partially branched.

With this aggregate board 20, second inner layer wiring patterns 42, which are formed by the fifth conductive layer 5 disposed from the front face Aa of the upper layer A of the insulator 9 to the rear face Bb of the lower layer B, have branched parts 42b at a part extending in the row direction, that is, at one end that is split so as to span first inner layer wiring patterns 41. In other words, part of the second inner layer wiring patterns 42 is branched so as to span between regions that are adjacent in the row direction, in the mounting region 9a of a single light emitting element.

Figure 2B:
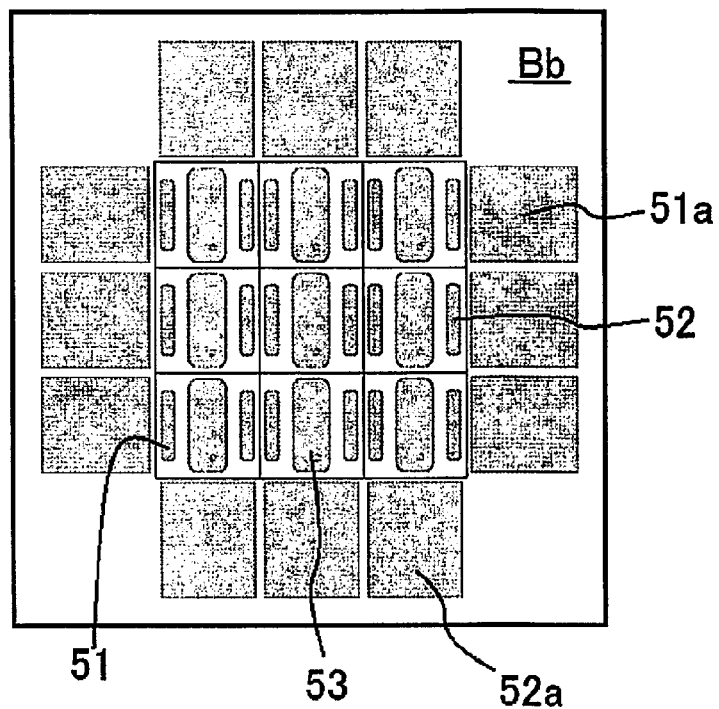
FIG. 2B is a plan view of the rear face of the aggregate board in FIG. 2A.

As shown in FIG. 2B, with branching of the second inner layer wiring patterns 42, the second rear face wiring patterns are split in two (52 and 53) at the rear face Bb of the lower layer B corresponding to these branched parts 42b, with one second rear face wiring pattern 53 being connected to the end of the branched parts 42b by the seventh conductive layer 7, and the other second rear face wiring pattern 52 being connected by the seventh conductive layer 7 to the second inner layer wiring pattern 42 that is not the branched parts 42b.

In order to increase the surface area accounted for by the second inner layer wiring patterns 52 and 53 at the rear face Bb of the lower layer B, the surface area accounted for by the rear face Bb of the lower layer B of the first rear face wiring pattern 51 is reduced. The second rear face wiring pattern 53 is such that if the aggregate board is cut in the mounting region of a single light emitting element, the first front face wiring pattern and the second front face wiring pattern will not be connected, so this functions as a heat dissipation member.

This configuration has the same function and effect as the aggregate board in Embodiment 1.

Embodiment 3

Aggregate Board

Figure 3A:
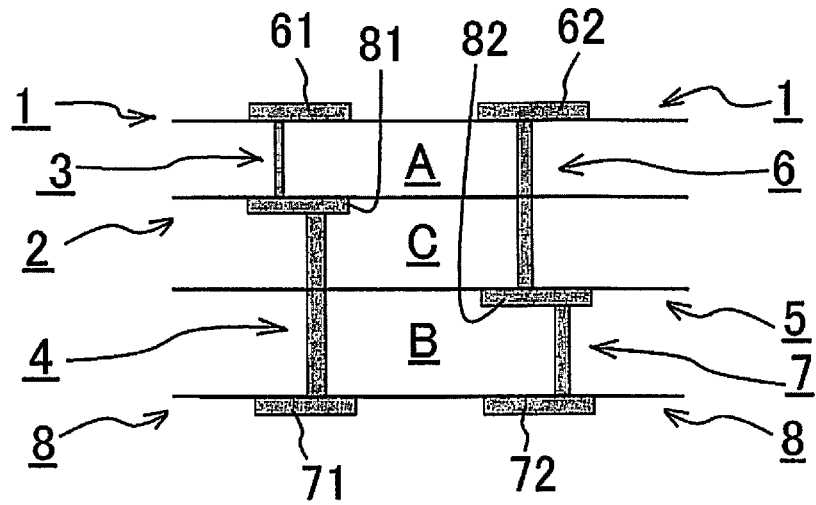
FIG. 3A is a partial cross section of the layer structure in another example of the aggregate board of the present disclosure.

As shown in FIG. 3A, the aggregate board 30 in this embodiment is such that the insulator has three layers: the upper layer A, a middle layer C, and the lower layer B. This aggregate board 30 has the various wiring patterns paired up in the mounting region of a single light emitting element, and a plurality of these units are arranged in a matrix (such as 3×3).

As in FIG. 1C, pairs of first front face wiring patterns 61 and second front face wiring patterns 62 that are arranged in a matrix are provided to the front face of the upper layer A of the insulator. The first front face wiring patterns 61 and the second front face wiring patterns 62 are constituted by the first conductive layer 1.

As in FIG. 1E, pairs of first rear face wiring patterns 71 and second rear face wiring patterns 72 that are arranged in a matrix corresponding to the first front face wiring patterns 61 and the second front face wiring patterns 62, respectively, are provided to the rear face of the lower layer B of the insulator. The first rear face wiring patterns 71 and the second rear face wiring patterns 72 are constituted by the eighth conductive layer 8.

First inner layer wiring patterns 81 and second inner layer wiring patterns 82 are arranged from the front face of the upper layer A of the insulator to the rear face of the lower layer B. The middle layer C is disposed between the upper layer A and the lower layer B.

The first inner layer wiring patterns 81 is disposed between the rear face of the upper layer A and the front face of the middle layer C. The first inner layer wiring patterns 81 has a second conductive layer 2 that extends in the column direction, a third conductive layer 3 that extends from this second conductive layer 2 toward the first conductive layer 1 and that is disposed in the interior of the upper layer A, and a fourth conductive layer 4 that extends from the second conductive layer 2 toward the eighth conductive layer 8 and that passes through the interior of the middle layer C and the lower layer B. With this configuration, the first inner layer wiring patterns 81 are connected to the first front face wiring patterns 61 and the first rear face wiring patterns 71, and are separated from the second front face wiring patterns 62 and the second rear face wiring patterns 72.

Figure 3B:
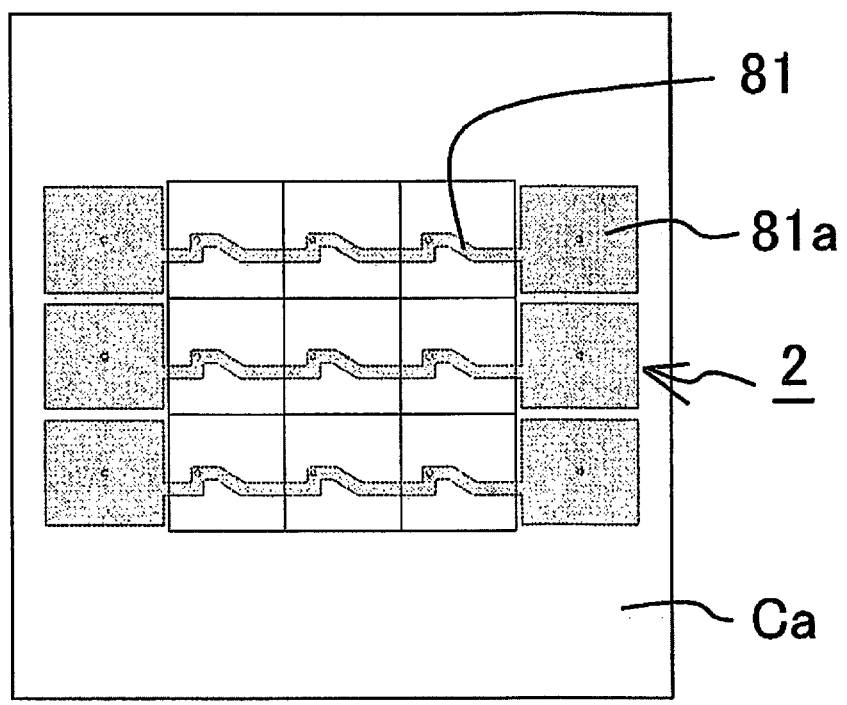
FIG. 3B is a plan view of the inner layer wiring pattern of the aggregate board.

As shown in FIG. 3B, of the first inner layer wiring patterns 81, the second conductive layer 2 is disposed on the front face Ca of the middle layer C, for example, and three lines are mutually separated and extend in the column direction (the first direction).

Wider regions 81a are disposed at both ends of the first inner layer wiring patterns 81.

The second inner layer wiring patterns 82 is disposed between the front face of the middle layer C and the front face of the lower layer B. The second inner layer wiring patterns 82 has a fifth conductive layer 5 that extends in the row direction, a sixth conductive layer 6 that extends from this fifth conductive layer 5 toward the first conductive layer 1 and that passes through the interior of the middle layer C and the upper layer A, and a seventh conductive layer 7 that extends from the fifth conductive layer 5 toward the eighth conductive layer 8 and that is disposed in the interior of the lower layer B. With this configuration, the second inner layer wiring patterns 82 are connected to the second front face wiring patterns 62 and the second rear face wiring patterns 72, and are separated from the first front face wiring patterns 61 and the first rear face wiring patterns 71.

Wider regions 82a are disposed at both ends of the second inner layer wiring patterns 82.

Figure 3C:
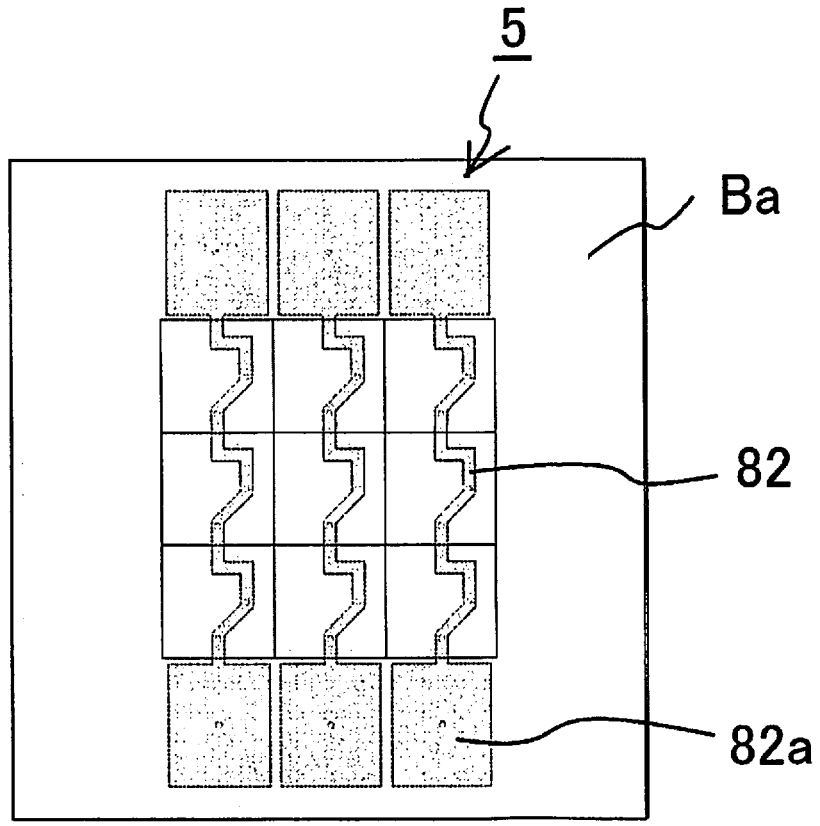
FIG. 3C is a plan view of the inner layer wiring pattern of the aggregate board.

As shown in FIG. 3C, of the second inner layer wiring patterns 82, the fifth conductive layer 5 is disposed at the front face Ba of the lower layer B, for example, and three lines are mutually separated and extend in the row direction (the second direction).

The wider regions at both ends in the second conductive layer and the fifth conductive layer, and the rear face pads at the rear face of the lower layer B are substantially the same as in the aggregate board 10. Other than the above, the configuration is substantially the same as that of the aggregate board 10 in Embodiment 1.

As shown in FIG. 1G the aggregate board thus configured features an extremely simple light emitting element mounting board, and positive and negative power supplies can be applied in column and row units without short-circuiting the positive and negative wiring patterns.

Embodiment 4

Aggregate Board

Figure 4:
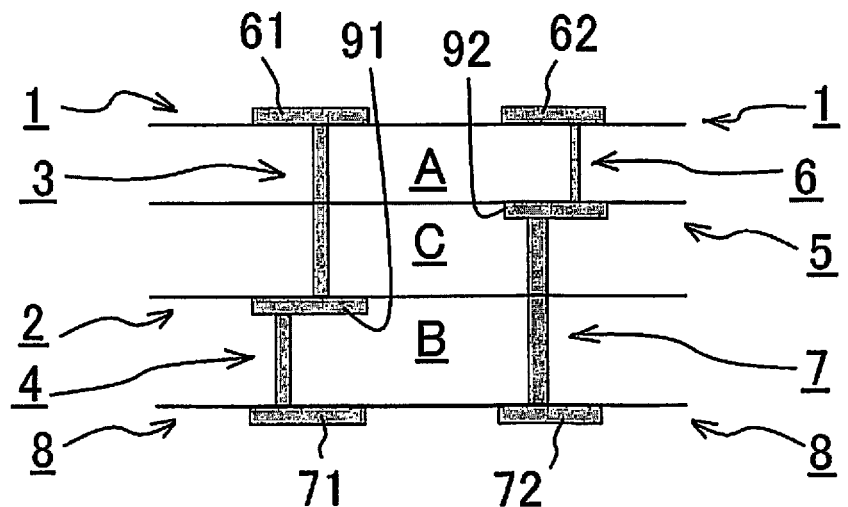
FIG. 4 is a partial cross section of the layer structure in another example of the aggregate board of the present disclosure.

As shown in FIG. 4, the aggregate board 40 in this embodiment is substantially the same as the aggregate board 30 in Embodiment 3 and the aggregate board 10 in Embodiment 1, except that the second conductive layer 2 and the fifth conductive layer 5 are laminated in reverse order on the front face and rear face of the middle layer C, and therefore the third conductive layer 3 passes through the middle layer C, the sixth conductive layer 6 passes through only the upper layer A, the fourth conductive layer 4 passes through only the lower layer B, and the seventh conductive layer 7 passes through the middle layer C, thereby configuring first inner layer wiring patterns 91 and second inner layer wiring patterns 92.

This configuration has the same function and effect as the aggregate boards in Embodiments 1 and 3.

Embodiment 5

Light Emitting Device

As shown in FIG. 5A, the light emitting device 60 in this embodiment comprises a fluorescent material layer 65, a reflective layer 66, a light emitting element 67, and a board 68 obtained from the above-mentioned aggregate board.

The board 68 is substantially flat and square on its top face, and has on its front face a conductive member 63b constituting first front face wiring pattern and second front face wiring pattern. On its rear face it has a conductive member 63c constituting first rear face wiring pattern and second rear face wiring pattern.

As discussed above, the first rear face wiring pattern is connected by the first inner layer wiring pattern, and the second rear face wiring pattern is connected by the second inner layer wiring pattern.

Figure 6A:
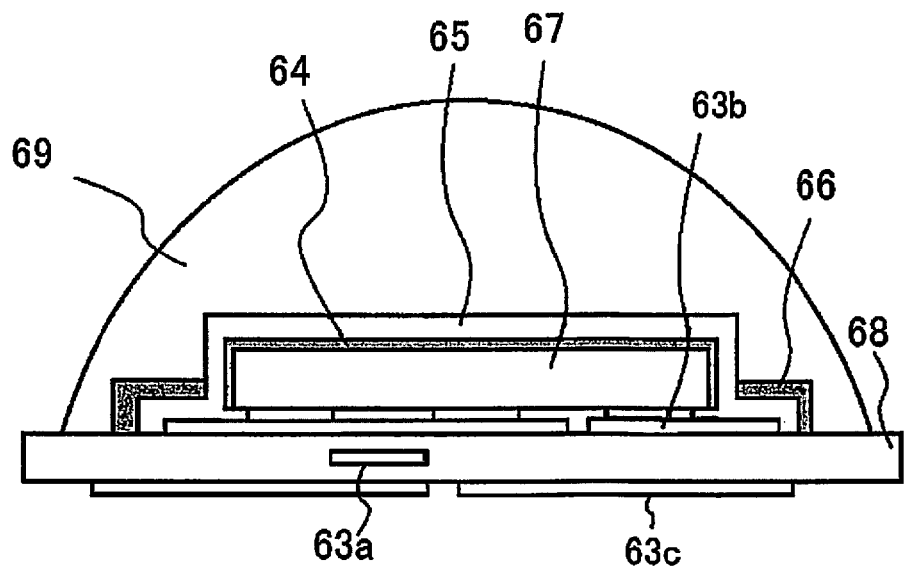
FIG. 6A is a simplified cross section of an example of the light emitting device of the present disclosure.
Figure 6B:
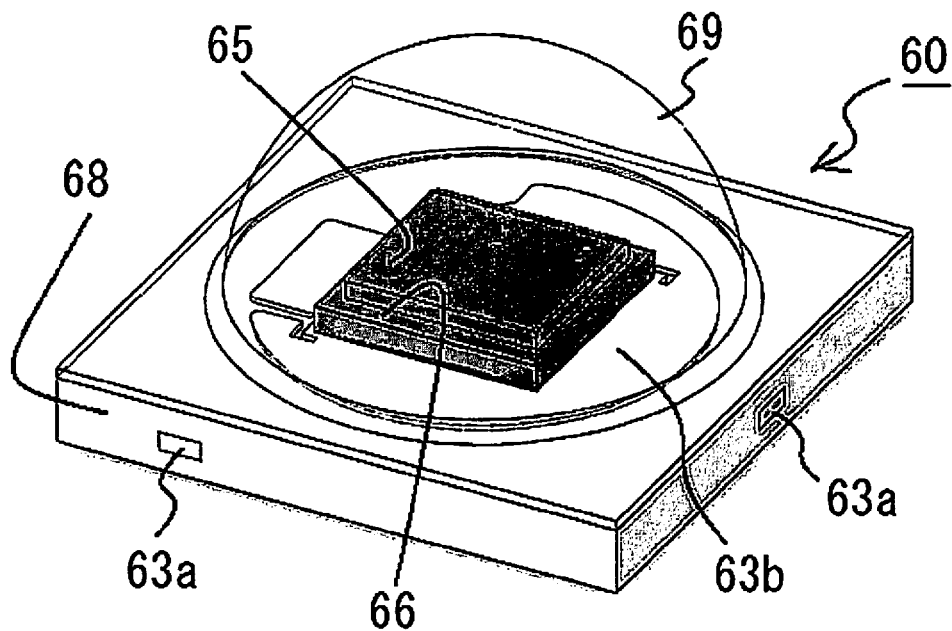
FIG. 6B is a simplified oblique view of an example of the light emitting device of the present disclosure.

The first inner layer wiring pattern and the second inner layer wiring pattern are exposed at their end faces at the same position (height) in the thickness direction of the board 68 (see 63a in FIGS. 5A and 6B). The first inner layer wiring pattern is exposed at a pair of end faces of the board 68 including two opposing edges, and the second inner layer wiring pattern is exposed at a pair of end faces of the board 68 including the other two opposing edges.

A light emitting element 67 is flip-chip mounted via Sn—Ag—Cu to the first front face wiring pattern and second front face wiring pattern of the board 68. The light emitting element 67 is disposed on the board 68 at the position shown in FIG. 5B.

A cover layer (aluminum film) 64 is formed as a thin-film on the side faces and the upper face (the face on the opposite side from the face opposing the board) of the light emitting element 67, and a fluorescent material layer 65 (containing YAG-based fluorescent material particles with an average particle size of 8 μm) is formed via this cover layer 64. The fluorescent material layer 65 is also formed over the conductive member 63 exposed on the peripheral edge of the light emitting element 67.

Further, a reflective layer 66 to which particles of $SiO_2$ (average particle size of 0.2 μm) have been affixed by electrodeposition is formed on the fluorescent material layer 65, around the light emitting element 67.

This light emitting device can be manufactured by the following method.

First, the above-mentioned aggregate board is prepared, and a plurality of light emitting elements are connected over the front face wiring pattern via a joining member (such as solder).

Next, a fluorescent material layer is formed so as to cover the light emitting elements on the aggregate board. The fluorescent material layer is formed at a location including the front face wiring patterns exposed around the light emitting elements.

For example, a solution containing a fluorescent material (an electrodeposition solution) is prepared, the light emitting elements are dipped in this, and voltage is applied to the light emitting elements themselves to deposit the charged fluorescent material particles on the light emitting elements by electrophoresis. If a sapphire substrate is disposed on the front face of the light emitting elements, a conductive cover layer may be formed over this front face, and voltage then applied to this cover layer.

After this, a reflective layer is formed around the light emitting elements. The reflective layer can be deposited via the fluorescent material layer on the conductive part around the light emitting elements by disposing the light emitting device in a solution containing the reflective material that constitutes the reflective layer, and subjecting the charged reflective material in the solution to electrophoresis.

Finally, the aggregate board is split up along the regions where each light emitting element is mounted, to obtain the light emitting devices 60.

With the above-mentioned light emitting device 60, after the reflective layer is formed, a convex lens 69 that covers the upper part of the light emitting element may be formed, for example, from a translucent material, by potting, compression molding, transfer molding, or the like, as shown in FIGS. 6A and 6B.

Also, with the above-mentioned light emitting device 60, a translucent resin layer 70 may be laminated over the entire surface of the fluorescent material layer 65 and the reflective layer 66 to protect these layers, resulting in the light emitting device 60a shown in FIG. 7A. This translucent resin layer 70 has a convex shape in which the center portion is thicker than the surrounding parts. The reliability of the resulting light emitting device can be improved by this configuration and additional steps.

Embodiment 6

Method for Testing Light Emitting Elements

As indicated in Embodiment 5, a plurality of light emitting elements are connected to the paired first and second front face wiring patterns on the aggregate board.

Consequently, individual light emitting elements can be lighted by applying a power supply to the aggregate board. This allows the illuminating characteristics and so forth of the light emitting elements to be tested for the aggregate board as a whole, in a group of light emitting elements, or for just one light emitting element.

In particular, if the fluorescent material layer that covers the light emitting elements is formed as discussed above after the light emitting elements have been mounted on the aggregate board, the light emitting elements can be lighted one at a time to measure how well the fluorescent material layer adheres, that is, the color of the light emitting elements produced by the fluorescent material layer, one by one.

Consequently, if the fluorescent material layer does not adhere well, an additional fluorescent material layer (65a in FIG. 7B) can be provided by dispenser coating with a solution containing a fluorescent material, for example, at just the light emitting elements in a state in which they have been mounted on the aggregate board.

As a result, light emitting elements having uniform characteristics can be manufactured over an entire aggregate board, which allows a higher yield to be achieved.

The light emitting device obtained after testing by this method is finished is the light emitting device 60b shown in FIG. 7B, in which an additional fluorescent material layer 65a (54 μm thick) is provided to the above-mentioned light emitting device 60. In this case, since forming the fluorescent material layer 65 and the reflective layer 66 by electrodeposition, etc., results in brittleness with respect to the air pressure that is attendant with the film formation method, a translucent resin layer 70 (36 μm thick) composed of silicone resin is formed before the formation of the additional fluorescent material layer 65a, for the purpose of reliably avoiding separation or deformation of the fluorescent material layer 65 and the reflective layer 66. This translucent resin layer 70 has a convex shape in which the center portion is formed thicker than the surrounding portion, and the additional fluorescent material layer 65a is also convex in shape.

That is, with the light emitting device 60a, the translucent resin layer 70 and the additional fluorescent material layer 65a are laminated in that order over the entire surface of the fluorescent material layer 65 and the reflective layer 66.

With this configuration and the addition of this step, light emitting devices having uniform characteristics can be manufactured, and the reliability of the light emitting devices thus obtained can be improved.

Alternatively, when the fluorescent material layer is formed and the reflective layer is then formed as discussed above, not only the adhesion of the fluorescent material layer, but also the luminance, brightness, and so forth of the light emitting elements can be measured individually by illuminating the light emitting elements one at a time.

Consequently, when the adhesion of a reflective layer is inadequate, a reflective layer can be added by coating just that light emitting element with a dispenser solution containing a reflective layer material, for example, after mounting on the aggregate board. As a result, light emitting elements having uniform characteristics throughout the entire aggregate board can be manufactured, and the yield can be raised.

INDUSTRIAL APPLICABILITY

The aggregate board of the present disclosure can be used to mount various kinds of electrical element, such as semiconductor elements and light emitting elements, and can be used for testing the operation in an aggregate state before splitting into the individual elements, testing flashing and so forth of electrical elements, and so on.

What is claimed is:

1. An aggregate board comprising:
an insulator having a front face and a rear face;
a plurality of pairs of a first front face wiring pattern and a second front face wiring pattern arranged on the front face of the insulator and respectively corresponding to a plurality of light emitting element mounting regions;
a plurality of pairs of a first rear face wiring pattern and a second rear face wiring pattern arranged on the rear face of the insulator;
at least one first inner layer wiring pattern that is separated from each of the pairs of the second front face wiring pattern and the second rear face wiring pattern, that is connected to at least one of the pairs of the first front face wiring pattern and the first rear face wiring pattern, and that has a part that extends in a first direction in an interior of the insulator;
at least one second inner layer wiring pattern that is separated from each of the pairs of the first front face wiring pattern and the first rear face wiring pattern, that is connected to at least one of the pairs of the second front face wiring pattern and the second rear face wiring pattern, and that has a part that extends in a second direction, which is different from the first direction as viewed along a direction normal to the front face of the insulator, in the interior of the insulator; and the first inner layer wiring pattern and the second inner layer wiring pattern being positioned in the same layer.

2. The aggregate board according to claim 1, wherein the first inner layer wiring pattern or the second inner layer wiring pattern is partially branched.

3. The aggregate board according to claim 2, wherein the first inner layer wiring pattern is branched in a region corresponding to the region passing over the pair of the first rear face wiring pattern and the second rear face wiring pattern that are mutually adjacent in the row direction, and/or the second inner layer wiring pattern is branched in a region corresponding to the region passing over the pair of the first rear face wiring pattern and the second rear face wiring pattern that are mutually adjacent in the column direction.

4. The aggregate board according to claim 1, wherein the first front wiring pattern and the second front wiring pattern are constituted by a first conductive layer, the first rear wiring pattern and the second rear wiring pattern are constituted by a eighth conductive layer, the first inner layer wiring pattern is constituted by a second conductive layer that extends in the first direction, a third conductive layer that extends from the second conductive layer and towards the first conductive layer, and a fourth conductive layer that extends from the second conductive layer and toward the eighth conductive layer, and the second inner layer wiring pattern is constituted by a fifth conductive layer that extends in the second direction, a sixth conductive layer that extends from the fifth conductive layer and towards the first conductive layer, and a seventh conductive layer that extends from the fifth conductive layer toward the eighth conductive layer.

5. The aggregate board according to claim 1, wherein the insulator has two or more of layers together.

6. The aggregate board according to claim 1, wherein the first rear wiring pattern and the second rear wiring pattern each have wide regions at both ends.

7. The aggregate board according to claim 1, wherein the insulator is a co-fired ceramics.

8. The aggregate board according to claim 1, wherein the insulator is a co-fired ceramics.

9. A method for testing a light emitting element, comprising the steps of:

connecting a plurality of light emitting elements to the pairs of first and second front face wirings of the aggregate board according to claim 1; and illuminating at least one light emitting element to test the characteristics of the light emitting element.

10. An aggregate board comprising:

an insulator having a front face and a rear face;

a plurality of pairs of a first front face wiring pattern and a second front face wiring pattern arranged on the front face of the insulator and respectively corresponding to a plurality of light emitting element mounting regions;

a plurality of pairs of a first rear face wiring pattern and a second rear face wiring pattern arranged on the rear face of the insulator;

at least one first inner layer wiring pattern that is separated from each of the pairs of the second front face wiring pattern and the second rear face wiring pattern, that is connected to at least one of the pairs of the first front face wiring pattern and the first rear face wiring pattern, and that a part that extends in a first direction in an interior of the insulator;

at least one second inner layer wiring pattern that is separated from each of the pairs of the first front face wiring pattern and the first rear face wiring pattern, that is connected to at least one of the pairs of the second front face wiring pattern and the second rear face wiring pattern, and that has a part that extends in a second direction, which is different from the first direction as viewed along a direction normal to the front face of the insulator, in the interior of the insulator; and the first rear wiring pattern and the second rear wiring pattern each having wide regions at both ends.

11. The aggregate board according to claim 10, wherein the first inner layer wiring pattern and the second inner layer wiring pattern are positioned in the same layer.

12. The aggregate board according to claim 10, wherein the first inner layer wiring pattern or the second inner layer wiring pattern is partially branched.

13. The aggregate board according to claim 12, wherein the first inner layer wiring pattern is branched in a region corresponding to the region passing over the pair of the first rear face wiring pattern and the second rear face wiring pattern that are mutually adjacent in the row direction, and/or the second inner layer wiring pattern is branched in a region corresponding to the region passing over the pair of the first rear face wiring pattern and the second rear face wiring pattern that are mutually adjacent in the column direction.

14. The aggregate board according to claim 10, wherein the first front wiring pattern and the second front wiring pattern are constituted by a first conductive layer, the first rear wiring pattern and the second rear wiring pattern are constituted by a eighth conductive layer, the first inner layer wiring pattern is constituted by a second conductive layer that extends in the first direction, a third conductive layer that extends from the second conductive layer toward the first conductive layer, and a fourth conductive layer that extends from the second conductive layer toward the eighth conductive layer, and the second inner layer wiring pattern is constituted by a fifth conductive layer that extends in the second direction, a sixth conductive layer that extends from the fifth conductive layer and towards the first conductive layer, and a seventh conductive layer that extends from the fifth conductive layer and toward the eighth conductive layer.

15. A light emitting device comprising:

a board having a plurality of wiring patterns and an insulator having a front face and a rear face;

a light emitting element that is mounted on the board; and a fluorescent material layer that covers the light emitting element, the wiring patterns including:

a pair of a first front face wiring pattern and a second front face wiring pattern disposed on the front face of the insulator;

a pair of a first rear face wiring pattern and a second rear face wiring pattern disposed on the rear face of the insulator;

a first inner layer wiring pattern that is connected to the first front face wiring pattern and the first rear face wiring pattern, and a second inner layer wiring pattern that is connected to the second front face wiring pattern and the second rear face wiring pattern;

the first inner layer wiring pattern and the second inner layer wiring pattern being positioned in the same layer; and the first inner layer wiring pattern is exposed at one pair of opposing end faces of the insulator, and the second inner layer wiring pattern is exposed at the other pair of opposing end faces of the insulator.

16. The light emitting device according to claim 15, wherein the fluorescent material layer covers the first front face wiring pattern and the second front face wiring pattern, and thickness of the fluorescent material layer disposed on the first front face wiring pattern is different from thickness of the fluorescent material layer disposed on the second front face wiring pattern.

17. The light emitting device according to claim 15, wherein a transparent resin layer covers over at least a portion of the fluorescent material layer.

18. The light emitting device according to claim 17, wherein the transparent resin layer has an upper face protruding upwardly.

19. The light emitting device according to claim 17, wherein an additional fluorescent material layer is disposed on the transparent resin layer.

20. The light emitting device according to claim 19, wherein the transparent resin layer is thinner than the additional fluorescent material layer.

* * * * *